US009829452B2

United States Patent
Orazem et al.

(10) Patent No.: US 9,829,452 B2
(45) Date of Patent: Nov. 28, 2017

(54) CORROSION DETECTION IN STRUCTURAL TENDONS

(71) Applicant: University of Florida Research Foundation, Inc., Gainesville, FL (US)

(72) Inventors: Mark E. Orazem, Gainesville, FL (US); Yu-Min Chen, Gainesville, FL (US); Christopher Alexander, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 292 days.

(21) Appl. No.: 14/509,221

(22) Filed: Oct. 8, 2014

(65) Prior Publication Data

US 2015/0097589 A1    Apr. 9, 2015

Related U.S. Application Data

(60) Provisional application No. 61/888,032, filed on Oct. 8, 2013, provisional application No. 61/947,594, filed on Mar. 4, 2014.

(51) Int. Cl.
*G01N 27/02* (2006.01)
*G01N 17/04* (2006.01)

(52) U.S. Cl.
CPC ............. *G01N 27/02* (2013.01); *G01N 17/04* (2013.01)

(58) Field of Classification Search
CPC .............................. G01N 27/02; G01N 17/04
(Continued)

(56) References Cited

U.S. PATENT DOCUMENTS 5,855,721 A * 1/1999 Monteiro ................. G01V 3/06
156/272.2
8,278,949 B2 10/2012 Buchler
(Continued)

FOREIGN PATENT DOCUMENTS

| EP | 0705422 | 2/1999 |
|---|---|---|
| EP | 1957957 | 5/2009 |
| NO | 2012087329 | 6/2012 |

OTHER PUBLICATIONS

Dr. Minchin; Florida Dept. of Transportation; "Identification and Demonstration of a Tech. Adaptable to Locating Water in Post-tensioned Bridge Tendons"; The University of Florida, Dec. 29, 2006; 52 pages.
(Continued)

*Primary Examiner* — Farhana Hoque
(74) *Attorney, Agent, or Firm* — Thomas | Horstemeyer LLP; Christopher B. Linder; Randy R. Schoen

(57) ABSTRACT

Various examples are provided for corrosion detection in structural tendons. In one example, among others, a method includes injecting current through a portion of a tendon assembly including a tendon at least partially encased in grout, where the current is injected through the portion of the tendon assembly via contact points on a surface of the grout. A potential across the portion of the grout surface is measured and a condition of the tendon can be based at least in part upon the current and the potential. In another example, a system includes supply electrodes to inject current into grout surrounding a tendon via contact with a surface of the grout, sensor electrodes to measure a potential difference between the supply electrodes, and an impedance detection device to determine an impedance of the tendon based at least in part upon the injected current and the potential difference.

14 Claims, 27 Drawing Sheets

(58) Field of Classification Search
USPC .................................. 324/693, 870.07, 536
See application file for complete search history.

(56) References Cited

U.S. PATENT DOCUMENTS

| | | | | |
|---|---|---|---|---|
| 2002/0154029 | A1* | 10/2002 | Watters | G01D 5/48 340/870.07 |
| 2010/0213079 | A1* | 8/2010 | Willis | A61B 5/14532 205/775 |
| 2011/0093219 | A1* | 4/2011 | Parker | G01B 11/03 702/34 |
| 2011/0191045 | A1* | 8/2011 | Boenisch | G01N 27/902 702/65 |
| 2012/0177448 | A1* | 7/2012 | Steyn | E21D 20/028 405/259.5 |
| 2013/0037420 | A1 | 2/2013 | Funahashi | |

OTHER PUBLICATIONS

Virmani; "Literature Review of Chloride Threshold Values for Grouted Post-Tensioned Tendons"; FHWA Publication No.: FHWA-HRT-12-067; FHWA Contacts: Paul Y. Virmani, HRDI-60, (202) 493-3052, paul.virmani@dolgov; Hamid Ghasemi, 16 pages. Long-Term Bridge Performance Program.

Lianfang Li, A.A. Sagüés, "Effect of Chloride Concentration on the Pitting and Repassivation Potentials of Reinforcing Steel in Alkaline Solutions," Corrosion, 99, No. 567, (1999).

C. Andrade, F. Bolzoni, "Measurement of Steel Corrosion in Concrete by Electrochemical Techniques: Influence of the Redox Processes in Oxide Scales"; Institute of Construction Sciences "Eduardo Torroja", CSIC, Apdo. 19002, Madrid, Spain Tolitecnico di Milano, Dipartamento di Chimica Fisica Applicata, Via Mancinelli, 7, 20131 Milano, Italy Universidade de Vigo. E.T.S.E. I.M., Lagoas-Marcosende, 9,36280 Vigo, Spain.

T.O. Mason; "Experimental limitations in impedance spectroscopy of cement-based materials; Advances in Cement Research", 1998, 10, No. 4, Oct.; pp. 143-150.

I. Martinez *, et al.; "Non-destructive electrochemical techniques applied to the corrosion evaluation of the liner structures in nuclear power plants"; Journal of Nuclear Materials 373 (2008) pp. 226-236.

M. Keddam, et al. "The concept of floating electrode for contactless electrochemical measurements: Application to reinforcing steel-bar corrosion in concrete"; Corrosion Science 51 (2009) pp. 1795-1801.

Kolluru V. Subramaniama; "Investigation of the local response of the steel-concrete interface for corrosion measurement"; Corrosion Science 51 (2009) pp. 1976-1984.

Azizinamini; "Improved Inspection Techniques for Steel Prestressing/Post-tensioning strand"; Jun., 2012; 111 pages.

A. Nogueira. Impedance Measurements in reinforced concrete and 3d fern stimulations:; Excerpt from the Proceedings of the COMSOL Multiphysics User's Conference 2005 Paris; 4 pages.

Michel Keddam et al.; "Impedance based method for non-contact determination of the corrosion rate in buried metallic structures"; EJECE—2011. Damage to structures, Paris France; pp. 1097-1103.

Keddam; Impedance measurements on cement paste: Cement and Concrete Research, vol. 27, No. 8, pp. 1191-1201.1997 Q Elsevier Science Ltd.

McKinstry; "Frequency Response of Damaged External Post-Tensioned Tendons; 2010"; The University of Texas at Austin; 155 pages.

D. D. Macdonald; "Evaluation of Electrochemical Impedance Techniques for Detecting Corrosion on Rebar in Reinforced Concrete"; SRI International Menlo Park, California; 93 pages; SHRP-ID/ UFR-91-524; 1994 National Academy of Sciences.

J.A. Gonzalez; "Electrochemical Techniques for Studying Corrosion of Reinforcing Steel: Limitations and Advantages"; Corrosion Science, vol. 61, No. 1.2005; 14 pages.

Carino; "Non-Destructive Techniques to investigate corrosion status in concrete structures"; 96 Journal of Performance of Constructed Facilities, Aug., 1999, 11 pages.

Andrade and Martinez; "Metal Corrosion Rate Determination of Different Solutions and Reinforced Concrete Specimens by Means of a Noncontacting Corrosion Method"; Corrosion Engineering Section; May, 2010; 10 pages.

Andrade; "Feasibility of determining corrosion rates by means of stray current-induced polarisation"; Journal Appl Electrochem (2008) 38: pp. 1467-1476.

Andrade; "non-contacting corrosion method applied to the steel corrosion rate determination in different solutions and reinforced concrete specimens"; Institute of Construction Science, CSIC, Madrid, Spain; 13 Pages.

Andrade; "Cement paste hardening process studied by impedance spectroscopy"; Electrochimica Acta 44 (1999) 4313-4318; Institute of Construction Sciences; 6 pages.

Andrade; "Analogue circuit of the inductive polarization resistance"; Institute of Construction Sciences, Eduardo Torroja, CSIC, C/ Serrano Galvache 4, 28033 Madrid, Spain; 7 pages.

Andrade; "Advances in Electrochemical Impedance Measurements in Reinforced concrete"; institute E. Torroja, CS.I. C., P.O. Box 19002, E-28080 Madrid, Spain; 15 pages.

Bartoli; Health monitoring to detect failure of prestressing PS cables in segmental boxgirder bridges' Department of Structural Engineering University of California, San Diego La Jolla, California 92093-0085; Sep., 2009; 132 pages.

Dr Donald Pearson-Kirk; the performance of post-tensioned bridges; Pearson-Kirk, Collard-Jenkins and Solan 2004 CBC; 13 pages.

Andrade; "The importance of geometrical considerations in the measurement of steel corrosion in concrete by means of AC impedance": Corrosion Science, vol. 37, No. 12, pp. 2013-2023, 1995.

Hassanein; "The use of small electrochemical perturbations to assess the corrosion of steel in concrete"; NDT&E International, vol. 31, No. 4, pp. 265-272, 1998.

Jieying Zhang; "Noninvasive Surface Measurement of Corrosion Impedance of Reinforcing Bar in Concrete—Part 3": Effect of Geometry and Material Properties; ACI Materials Journal/Jul.-Aug. 2004; 8 pages.

Subramaniam; et al. "Investigation of the local response of the steel—concrete interface for corrosion measurement"; corrosion Science 51 (2009) pp. 1976-1984.

Alsonso, et al.; "Study of the Dielectric Characteristics of Cement Paste"; Material Science Forum, vols. 289-292; 1998 Trans Tech Publications, Switzerland.

Sagues, et al.; "initial development of methods for assessing condition of post-tensioned tendons of segmental bridges"; University of South Florida; May 17, 2000; 39 pages.

John S. Popovis, Ph.D.; Denys Breysse, editor; "non-destructive assessment of concrete structures"; RILEM, 2012; 389 pages; University of Illinois.

Rafols, et al.; "Approach to Determine Corrosion Propensity in Post-Tensioned Tendons with Deficient Grout"; Open Journal of Civil Engineering, 2013, 3, 182-187 http://dx.doi.org/10.4236/ojce.2013.33022 Published Online.

Andrade and Gonzalez; "Quantitative measurements of corrosion rate of reinforcing steels embedded in concrete using polarization resistance measurements"; Werkstoffe and Korrosion 29, 515-519 (1978).

Koleva; "Quantitative characterisation of steel/cement paste interface microstructure and corrosion phenomena in mortars suffering from chloride attack"; Corrosion Science 48 (2006) 4001-4019.

Morris, et al.; "Practical evaluation of resistivity of concrete in test cylinders using a wenner array probe"; Cement and concrete Research, vol. 26, No. 12, pp. 1779-1787, 1996.

Powers, et al.; "Corrosion of post-tensioned tendons in Florida bridges"; Research Report No. FL/DOT/SMO/04-475; University of South Florida; 17 pages, year unknown.

Feliu; "Possibilities and problems of in situ techniques for measuring steel corrosion rates in large reinforced concrete structures"; Corrosion Science 47 (2005) 217-238.

(56) References Cited

OTHER PUBLICATIONS

Martinez; "Polarization resistance measurements of bars embedded in concrete with different chloride concentrations": EIS and DC comparison; Materials and Corrosion 2011, 62, No. 10; 11 pages.
Andrade, Gonzalez; "On-site detection of corrosion in reinforced concrete structures; Materials and Structures/ Matriaux et Constructions"; 1991, 24, 346-350.
Jieying Zhang; "Noninvasive Surface Measurement of Corrosion Impedance of Reinforcing Bar in Concrete—Part 2": Forward Modeling; ACI Materials Journal/May-Jun. 2002; 8 pages.
Jieying Zhang; "Noninvasive Surface Measurement of Corrosion Impedance of Reinforcing Bar in Concrete—Part 1": Forward Modeling; ACI Materials Journal/May-Jun. 2002; 10 pages.
Sadowski; "New non-destructive method for linear polarisation resistance corrosion rate measurement"; Archives of civil and mechanical engineering; vol. X, 2010, 8 pages.
S. Feliu, "Multiple-electrode method for estimating the polarization resistance in large structures"; Journal of Applied Electrochemisty; (1996) pp. 305-309.
Paulo J. M. Monteiro, et al. "Nondestructive Measurement of Corrosion State of Reinforcing Steel in Concrete"; ACI Materials Journal/Nov.-Dec. 1998; 6 pages.
Feliu: "Modelling of the steel—concrete interface to obtain information on reinforcement bar corrosion"; Journal of Applied Electrochemistry (2005) 35: pp. 429-436.

* cited by examiner

| Cl concentration<br>Sweep Rate | 0.53M (3 wt%) | 0.68M |
|---|---|---|
| 5mV/s | No pitting | Pitting |
| 10mV/s | No pitting | Pitting |
| 50mV/s | No pitting | Pitting |

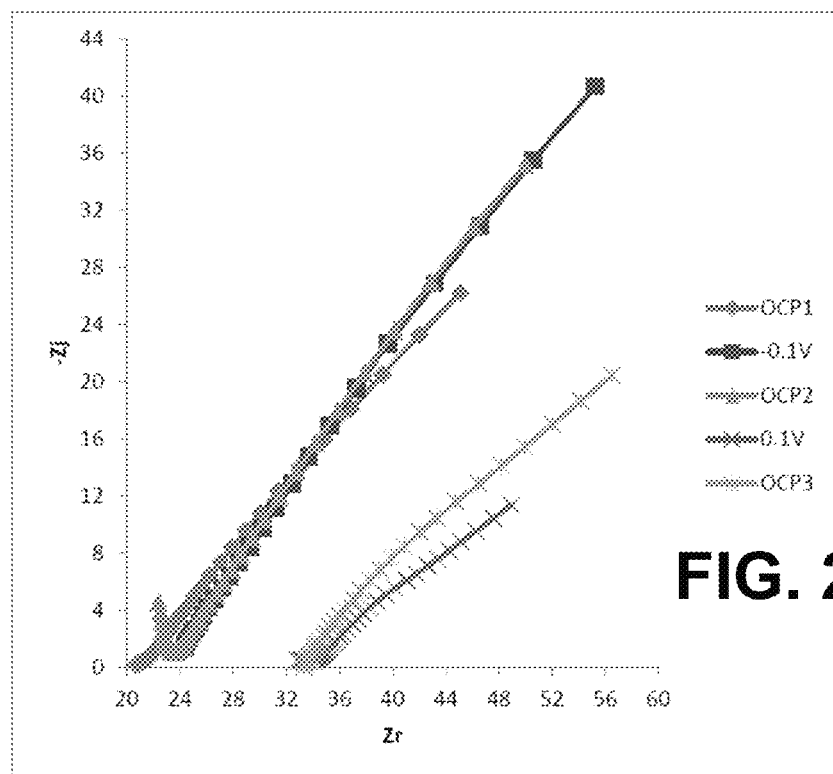
FIG. 26
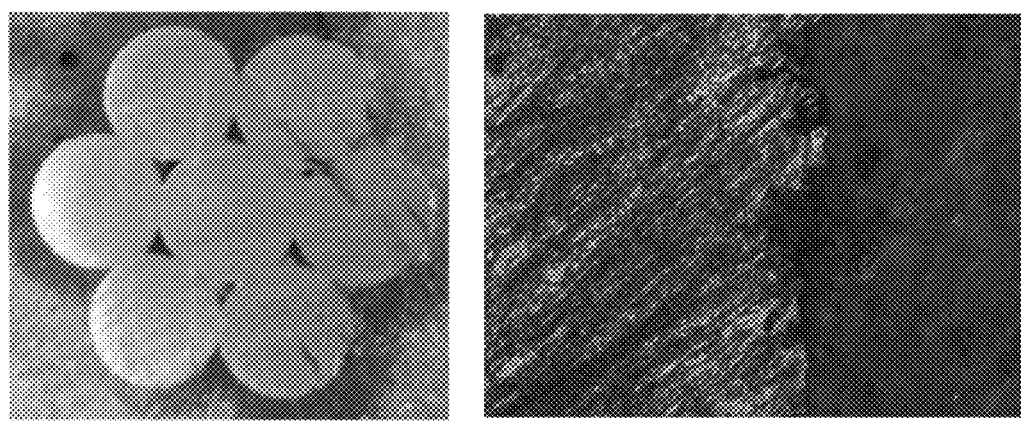
(a)  FIG. 27  (b)

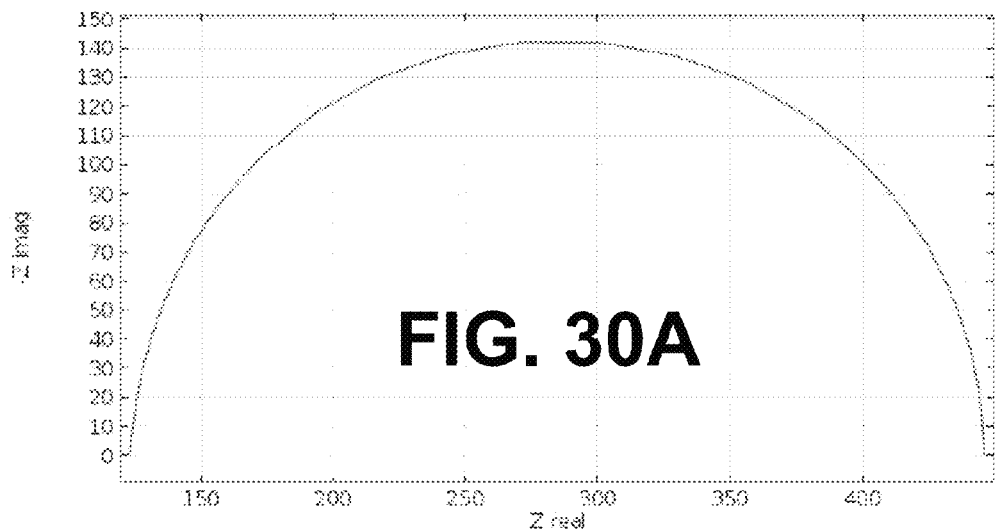
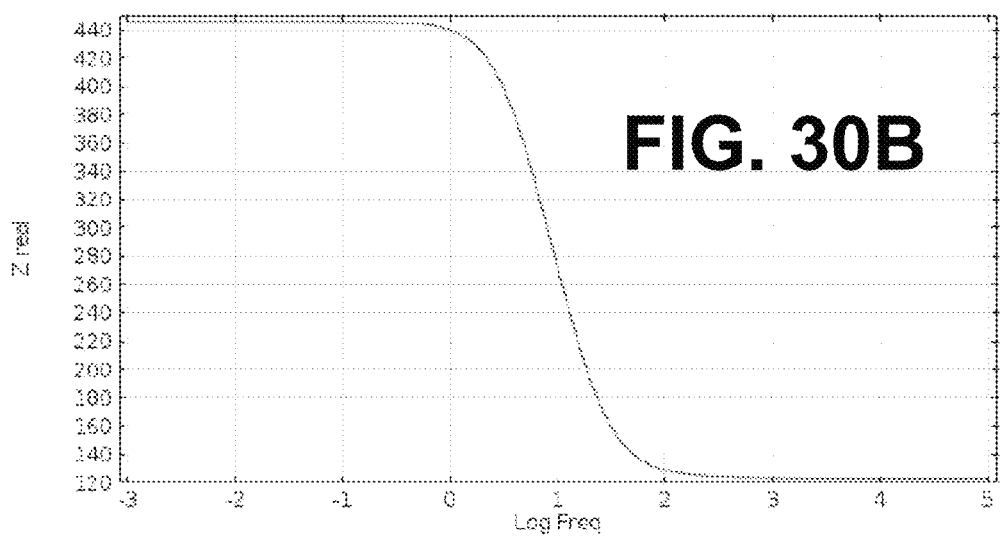
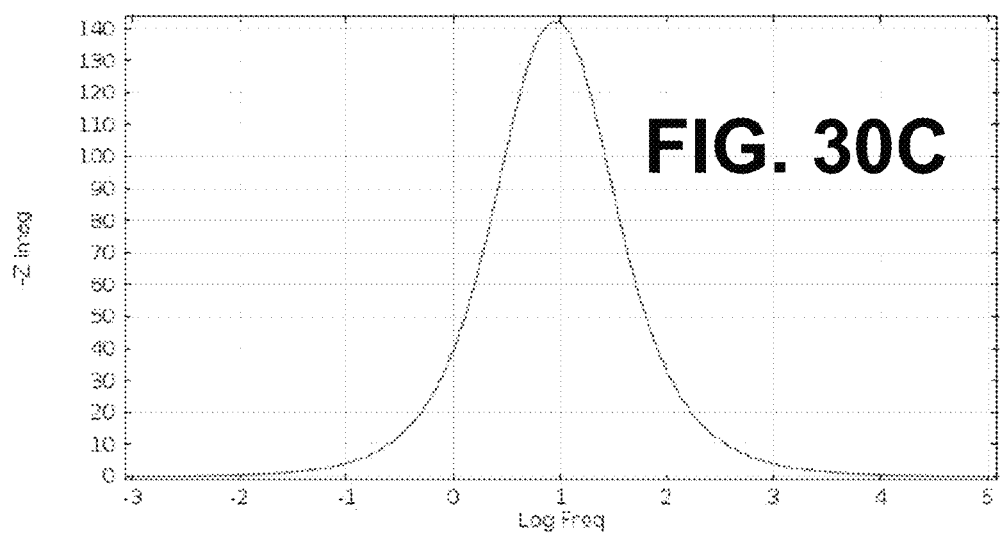

CORROSION DETECTION IN STRUCTURAL TENDONS

CROSS REFERENCE TO RELATED APPLICATIONS

This application claims the benefit of and priority to U.S. provisional application entitled "CORROSION DETECTION IN STRUCTURAL TENDONS" having Ser. No. 61/888,032, filed Oct. 8, 2013 and U.S. provisional application entitled "CORROSION DETECTION IN STRUCTURAL TENDONS" having Ser. No. 61/947,594, filed Mar. 4, 2014, both of which are hereby incorporated by reference in their entirely.

BACKGROUND

External post-tensioned tendons are structural elements used in segmental bridges to increase flexural capacity between spans and reduce stress cracking. Segmental bridge construction incorporating post-tensioned tendons allows for longer spans between piers and provides increased concrete durability. In this type of bridge construction, precast concrete box-girders are linked outward from bulkheads to form a bridge span between piers. The tendons are located within the inner opening of the box-girders and run continuously through deviator blocks, which help form the profile of the tendon. They include multiple 7-wire pre-stressing strands contained within a high density polyethylene (HDPE) duct. The ends of the tendons are anchored down and stressed after which the duct is filled with cementitious grout.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 16C, 17A-17B and 18B are plots of various characteristics of tendon assembly samples or specimens in accordance with various embodiments of the present disclosure.

FIGS. 21-26 and 28A-28B are plots of various characteristics of tendon assembly samples or specimens in accordance with various embodiments of the present disclosure.

FIG. 27 includes cross-sectional views illustrating corrosion of a tendon in accordance with various embodiments of the present disclosure.

FIGS. 30A-30C are plots of the impedance of the simulated tendon assembly of FIGS. 29A-29C in accordance with various embodiments of the present disclosure.

DETAILED DESCRIPTION

Figure 1:
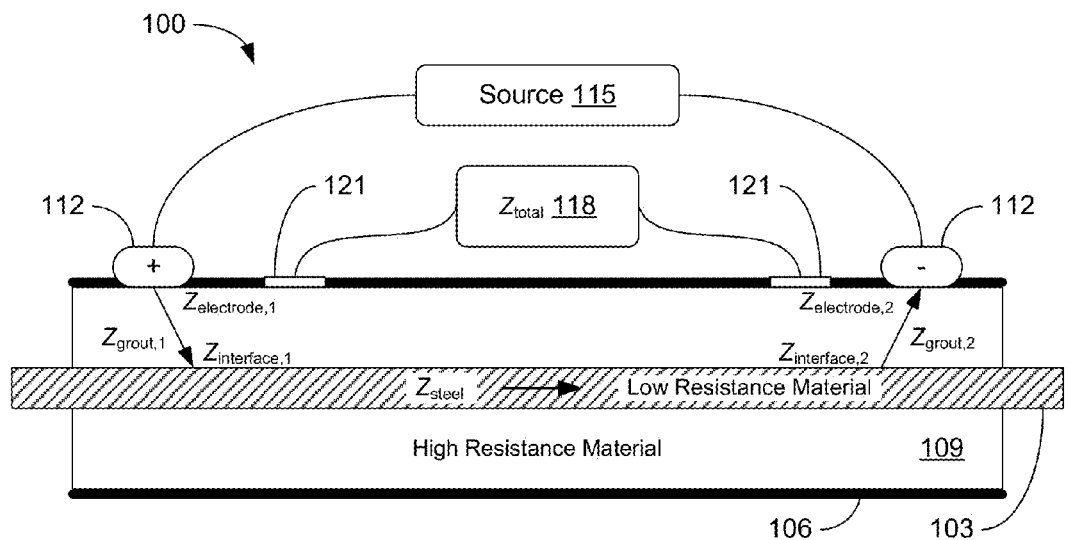
FIG. 1 is a graphical representation of an example of a corrosion detection system in accordance with various embodiments of the present disclosure.

Disclosed herein are various embodiments of systems and methods related to corrosion detection in structural tendons. Reference will now be made in detail to the description of the embodiments as illustrated in the drawings, wherein like reference numbers indicate like parts throughout the several views.

Tendon assemblies include multiple pre-stressing strands extending through a HDPE duct. The ends of the tendons are anchored and stressed, after which the duct is filled with grout. The alkaline grout is designed to provide protection against corrosion but, due to, possible voids in the grout and areas of improper mixing, cases of severe corrosion have occurred. In some cases, the steel strands within the tendons have completely corroded without external warning. Because post-tensioned concrete members rely on tensile strength or pre-stressed steel to resist loading, the loss of even a few strands could have catastrophic results.

For example, post-tensioned tendons are used in pre-cast concrete segmental bridge construction to increase flexural capacity and to prevent shear cracking. They can include 7-wire high strength pre-stressing steel strands surrounded by a cementitious grout and encased in a high density polyethylene (HDPE) duct. The grout, when mixed properly, has a high pH and provides an alkaline environment to protect the steel from corroding. However, there have been cases in which the steel strands have completely corroded through and failed without visual warning.

Non-destructive electrochemical impedance spectroscopy can be used to detect regions in which corrosion has compromised the strength of the cable without direct contact with the cable. Electrochemical impedance spectroscopy can indirectly polarize steel that is contained within an electrolytic media and determine its corrosive state. The difficulty lies in obtaining the true polarization resistance of the steel from the impedance of the whole system. A finite-element model has been developed to solve for the frequency-dependent potential distribution through a cylindrical grout specimen containing one axially-located steel strand. Impedance simulations were performed with different steel corrosion states while incorporating the kinetics at the current-injecting electrodes. The estimated polarization resistance of the steel can be over-estimated by as much as 13 percent if the electrode kinetics are not applied.

The loss of steel cross-sectional area in the stressed strands due to corrosion can lead to an abrupt failure that can cause residual damage to the surrounding structure. The corrosion state of steel is often quantified in terms of corrosion rate expressed in units of depth of material loss per unit time. The corrosion rate can be estimated with the use of the Stern-Geary relationship with the measurement of the steel polarization resistance. Conventional methods to obtain this parameter require electrical connection to the steel which is seldom available. An indirect impedance technique would allow the state of the steel within external post-tensioned tendons to be described without a direct connection to the steel.

Nondestructive techniques aim to evaluate and quantify the state of the steel without damaging the surrounding concrete, which can be costly. One method is magnetic flux leakage, which measures changes in an applied magnetic field caused by corrosion or fractures in the strands. Another method is ultrasonic tomography, which detects voids within the tendons by sending ultrasound waves and measuring the time for them to be transmitted. Differences in the density of the media can lead to longer transmission times. While these methods are useful in identifying problem areas, electrochemical techniques can yield corrosion rates of the tendons.

Electrochemical experiments can be used to measure the polarization resistance of a conducting material. The polarization resistance is used in the Stern-Geary relationship $$i_{corr} = B/A \cdot R_p, \qquad (1)$$

where B is a constant with units of mV, A is the area of the metal surface, and $R_p$ is the polarization resistance. The conventional method to measure the polarization resistance of reinforcing steel consists of a three electrode configuration that requires a connection to the steel to polarize it. Access to the steel is only possible by cutting through the concrete. A non-contact method has been developed in which an electric field is applied to the surface of the concrete and the induced current indirectly polarizes the steel. The slope of the polarization curve can be used to calculate the corrosion current ensuring that the applied polarization is small enough not to change any of the characteristics of the steel. The polarization resistance of the steel may be estimated from the resistance of the electrolyte and the resistance of the cell measured with the steel present. An equation for the estimation may be derived based on the assumption that the current ran parallel to the steel.

An alternative to the pulse method is electrochemical impedance spectroscopy, which uses a current or potential perturbation applied to the concrete surface at a range of frequencies to indirectly polarize the steel. Indirect impedance spectroscopy can be used to determine the location and the condition of steel rebar within concrete slabs. The measured surface impedance can be qualitatively determined to be a function of the corrosion state of the steel as well as the resistance of the concrete. Finite element models may be used to define an analogue circuit that accounts for the polarization behavior of the steel and the properties of the mortar in which the steel is embedded. The steel can be indirectly polarized using contact-less electrodes if the mortar resistivity is sufficiently large. Finite element modeling can also been used to simulate the indirect impedance. At low frequencies (DC limit), the current flows parallel to the steel; whereas, at high frequencies the current enters the steel perpendicularly. The zero frequency limit as a function of the applied polarization resistance, both scaled by the resistivity of the grout, can be independent of the grout resistivity for a defined geometry and electrode configuration. The impedance of the current-injection electrodes may be neglected. Accounting for the kinetics at the current injecting electrodes can improve the results. A mathematical development using electrode kinetics to model the boundary conditions at the steel interface as well as the current-injecting electrodes will be discussed. Simulated impedance results for a cylindrical grout specimen representing a section of a tendon with different grout resistivities, steel corrosion rates, and charge transfer resistances at the current-injecting electrodes will be presented and the effect of these parameters will be assessed.

Referring to FIG. 1, shown is an example of a system 100 for measuring corrosion in structural tendons. A tendon assembly includes a tendon 103 extending through a duct 106, which is filled with grout 109. The tendon 103 can be secured to anchor points at either end. Impedance measurements can be used to explore the behavior of the metal-grout interface, which the indirect impedance measurement is intended to quantify. Supply electrodes 112 in contact with the grout 109 surrounding the tendon 103 can be used to inject current provided by a power source 115 for impedance measurements. Using an impedance measurement device 118 such as, e.g., a potentiometer, the total impedance (Z total) can be measured at measurement points such as, e.g., sensor electrodes 121. As shown in FIG. 1, the impedance measured by the indirect technique can be described as:

$$Z_{total} = Z_{electrode,1} + Z_{grout,1} + Z_{interface,1} + Z_{steel} + Z_{interface,2} + Z_{grout,2} + Z_{electrode,2}, \qquad (2)$$

where $Z_{electrode}$ is the impedance at the supply electrode 112 contact interface with the grout 109, $Z_{grout}$ is the impedance of the grout 109, and $Z_{interface}$ is the impedance of interface between the grout 109 and the metal (e.g., steel) of the tendon 103. The subscripted number refers to the location at which the impedance is measured. The term $Z_{steel}$ includes the resistance to current flow in the metal of the tendon 103, which can normally be neglected. The supply electrodes 112 and/or sensor electrodes 121 may be, e.g., silver-silver chloride or other appropriate type of electrode material.

Access to the surface of the grout 109 can be established through small holes drilled into the duct 106. Electrodes can be placed into the holes with a conductive gel adhesive to ensure electrical contact to the grout 109. The impedance is measured with the four electrodes, working and counter (or supply) electrodes 112 and two reference (or sensor) electrodes 121. An alternating current over a range of frequencies is injected through the working electrode 112 and the potential difference is measured between two reference electrodes 121. The impedance is a function of frequency measured as the quotient of the potential difference between the reference electrodes 121 and the current at the working electrode 112. Since the steel of the tendon 103 has a much higher conductivity than the grout 106, the current is more likely to go through the steel. However, the amount of current that enters the steel depends on the distance between the current-injecting electrodes 112 relative to the depth to the tendon 103. There are two overall paths that the current can take. Either it will flow through the grout 106 and then the steel of the tendon 103, or it will go through the grout 106 without entering the steel of the tendon 103. Therefore, the measured impedance includes both the steel and grout properties with the resistivity of the grout 106 contributing to the overall impedance in both a series and parallel fashion. The steel surface impedance may be obtained from the total impedance measured and used to quantitatively describe the steel surface in terms of its corrosion rate or passive film thickness.

The impedance is the quotient of the potential difference measured between the sensor (or reference) electrodes 121 and the current perturbation applied between the supply (or current-injecting) electrodes 112 expressed as:

$$Z = \Delta V / \Delta I. \tag{3}$$

The potential distribution through the supply electrolytes 112:

$$V = \bar{V} + Re\{\tilde{V}e^{j\omega t}\}, \tag{4}$$

which includes a steady-state and an oscillating term, provides a physical meaning to the measured impedance.

The steady-state potential distribution through the grout 109 is determined by solving Laplace's equation. A potential difference is applied to the current-injecting electrodes 121 as 1V and −1V respectively to induce a DC current through the tendon assembly. At the steel-grout interface a steady-state current density based on the cathodic and anodic reactions is applied as:

$$\bar{i} = i_0 \left\{ \exp\left(\frac{(1-\alpha)nF}{RT} \eta_s\right) - \exp\left(-\frac{\alpha nF}{RT} \eta_s\right) \right\}, \tag{5}$$

where $i_0$ is the exchange current density, $\eta_S$ is the surface over-potential, F is Faraday's constant, R is the gas constant and T is the temperature.

The oscillating solution can also be found by solving Laplace's equation but with frequency-dependent boundary conditions. Linear kinetics may be used as the boundary condition on a disk electrode. The normal current density at the surface of the electrodes can be expressed in terms of a faradaic reaction and a charging current as:

$$i = C\frac{\partial(V-\Phi)}{\partial t} + \frac{(\alpha_a + \alpha_c)i_0 F}{RT}(V-\Phi) = -\kappa \frac{\partial \Phi}{\partial y}, \tag{6}$$

where κ is conductivity of the grout. The oscillating current density may be expressed in the frequency domain as:

$$\tilde{i} = j\omega C(\tilde{V} - \tilde{\Phi}) + \frac{(\alpha_a + \alpha_c)i_0 F}{RT}(\tilde{V} - \tilde{\Phi}). \tag{7}$$

where $\tilde{V}$ is the potential perturbation, $\tilde{\Phi}$ is the complex oscillating potential within the electrolyte, $\alpha_a$ and $\alpha_c$ are anodic and cathodic symmetry coefficients and with the use of the relationship:

$$i = \bar{i} + Re\{\tilde{i}e^{j\omega t}\}, \tag{8}$$

where the current is expressed as the addition of a steady-state and an oscillating term.

A positive potential perturbation was applied to the working electrode and a negative one was applied to the counter electrode. The potential perturbation at the steel interface was set to zero. The steel was modeled for an active corrosion case and a passive blocking electrode case. The active case, $$\tilde{i} = j\omega C(-\tilde{\Phi}) + \frac{(\alpha_a + \alpha_c)i_0 F}{RT}(-\tilde{\Phi}), \tag{9}$$

is expressed as the addition of the charging and faradaic current.

The passive case is modeled using a single Constant-Phase-Element (CPE) with an impedance of:

$$Z_{CPE} = \frac{1}{(j\omega)^\alpha Q}, \tag{10}$$

where the parameters α and Q as well as the phase angle are independent of frequency. When α=1, Q has units of capacitance. When α does not equal 1, the system has a distribution of time constants or surface heterogeneity either normal parallel to the surface. The expression used to represent blocking behavior at the steel for the normal current density of a CPE is:

$$\tilde{i} = -\tilde{\phi}\omega^\alpha Q\left[\cos\left(\alpha\frac{\pi}{2}\right) + j\sin\left(\alpha\frac{\pi}{2}\right)\right]. \tag{11}$$

The term, J, which is used in the impedance analysis, was defined as $$J = \frac{r_0 i_0 F(\alpha_a + \alpha_c)}{\kappa RT}, \tag{12}$$

where $r_0$, the characteristic length, was assumed to be the radius of the working electrode. This term can be expressed as a unit-less ratio of the ohmic resistance of the electrolyte and the charge-transfer resistance of the electrode as, $$J = \frac{\rho \times r_0}{R_t}. \tag{13}$$

where ρ is the resistivity of the grout. The charge-transfer resistance for linear kinetics can be expressed in terms of the exchange current density as:

$$R_t = \frac{RT}{i_0 F(\alpha_a + \alpha_c)}. \tag{14}$$

The three dimensional (3D) potential distribution was determined assuming a uniform conductivity electrolyte, and the indirect 4-point impedance was simulated. The effect of the charge-transfer resistance at the current injecting electrodes can be assessed and the actual polarization resistance of the steel from the indirect impedance may be determined.

Simulation of a tendon assembly including a tendon 103 surrounded by grout 109 was carried out. The simulated impedance uses the oscillating potential distribution response to calculate the 4-point indirect impedance for a given frequency range. The boundary conditions are applied to a two dimensional (2D) square as a proof of concept and then a 3D cylindrical specimen is modeled to represent a section of a tendon 103.

Figure 2:
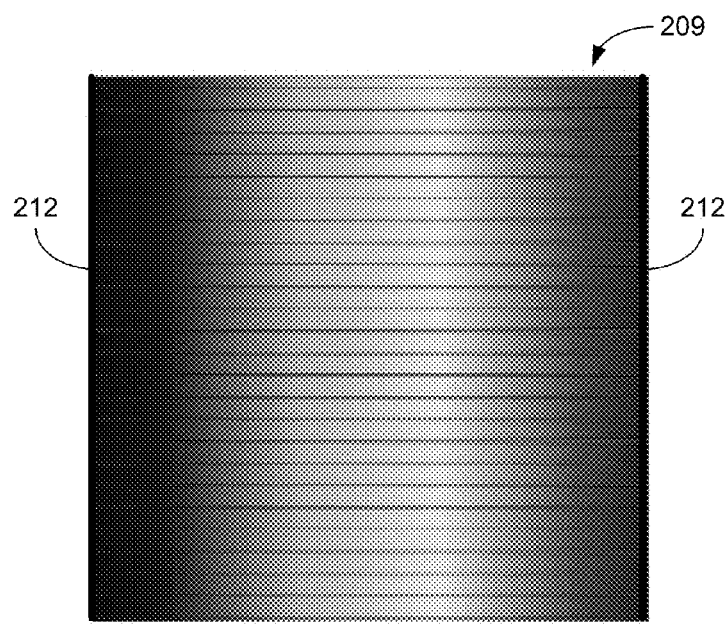
FIG. 2 is a graphical representation of an example of the current and potential distribution of a square grout model in accordance with various embodiments of the present disclosure.
Figure 3:
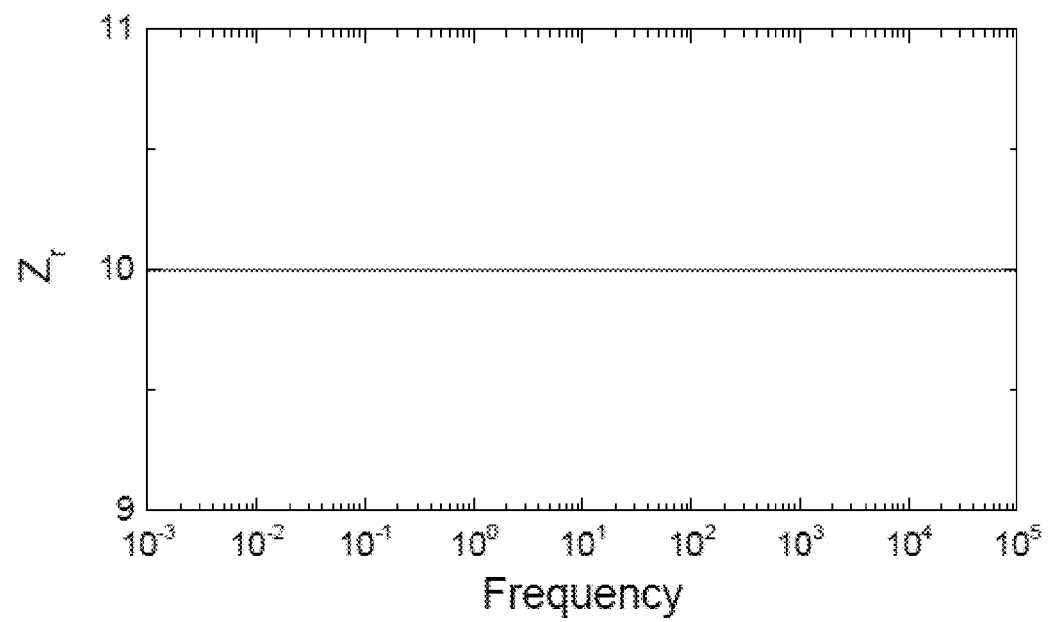
FIG. 3 is an example of a plot of the simulated real impedance of the square grout model of FIG. 2 as a function of frequency in accordance with various embodiments of the present disclosure.

Referring to FIG. 2, shown is a graphical representation of an example of the current and potential distribution of a 1 cm square 10 Ohm-m resistivity grout model 209 with current injecting (or supply) electrodes 212 placed on the vertical sides. A 2D square of uniform conductivity was modeled to confirm the oscillating current boundary conditions. The 2-point impedance was simulated by setting the vertical sides of the square as current-injecting electrodes 212 and calculating the potential difference across the grout electrolyte. FIG. 3 shows a plot of the simulated real impedance of the 1 cm square grout model 209 (FIG. 2) as a function of frequency. At all frequencies the real impedance is the resistivity of the grout electrolyte multiplied by the distance between the electrodes and divided by the cross sectional area. The imaginary impedance is zero since the grout 203 is modeled as a homogenous material with a constant resistance. The potential distribution is illustrated by the shading gradient in FIG. 2 and the current path is illustrated by the horizontal lines in FIG. 2.

Figure 4A:
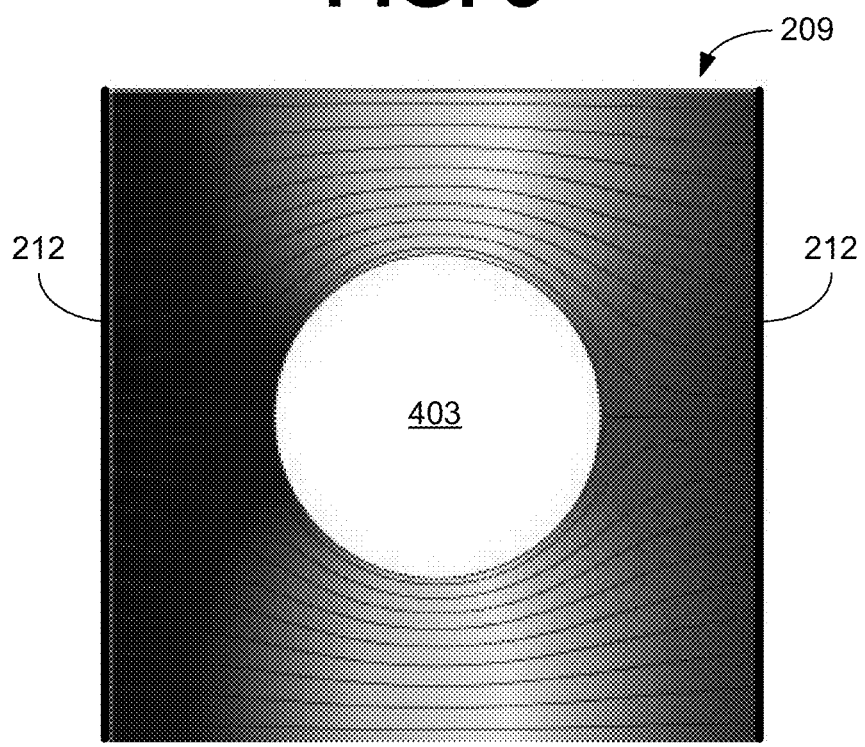
FIGS. 4A and 4B are graphical representations of examples of the current and potential distribution of a square grout model including a circular steel element in accordance with various embodiments of the present disclosure.
Figure 4B:
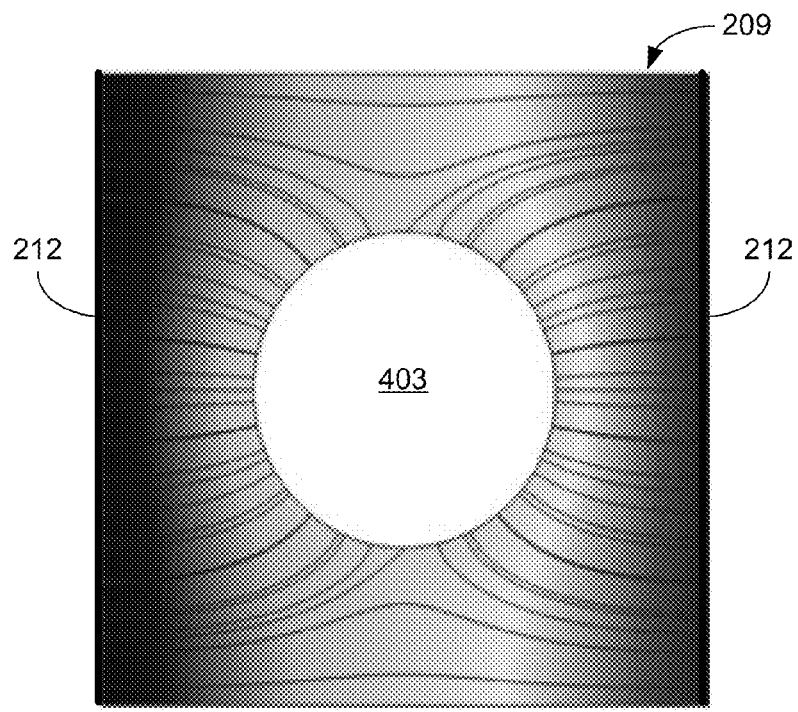

A circular steel element was inserted into the grout model with the actively corroding case described by EQN. 9. FIGS. 4A and 4B show graphical representations of examples of the current and potential distribution of the 1 cm square grout model 209 with a 0.25 cm radius circular steel element 403 placed in the center at the low frequency limit and the high frequency limit, respectively. At low frequencies, the circular steel element 403 behaves as an open circuit due to the dominance of the charge transfer resistance and repels the current as illustrated in FIG. 4A.

Figure 5:
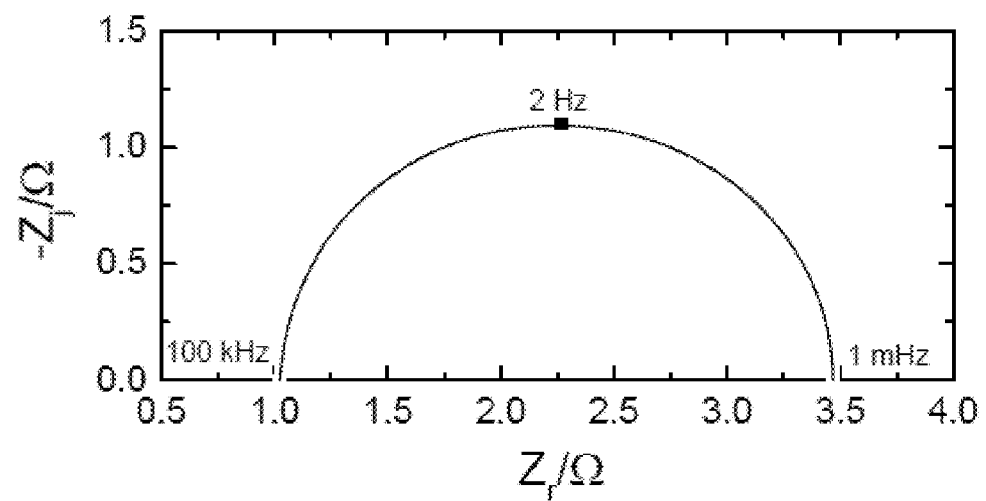
FIG. 5 is a plot of the simulated impedance of the square grout model with the circular steel element of FIGS. 4A and 4B in accordance with various embodiments of the present disclosure.

At high frequencies, the circular steel element 403 behaves as a closed-circuit and the current enters the circular steel element 403 normal to the surface as depicted in FIG. 4B. Referring to FIG. 5, shown is a plot of the simulated impedance of the 1 cm square grout model 209 with the 0.25 cm radius circular steel element 403 of FIGS. 4A and 4B. The Nyquist plot of the simulated impedance is a capacitive loop representative of an RC element.

Figure 6:
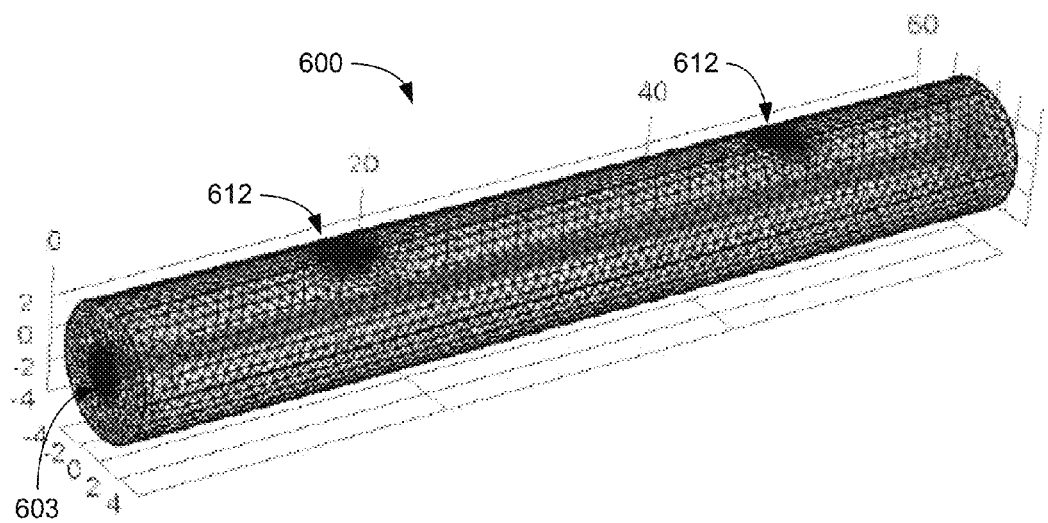
FIG. 6 is an example of a mesh model of a tendon assembly in accordance with various embodiments of the present disclosure.

A 60 cm long cylindrical section 600 of a tendon assembly was modeled in 3D, with and without steel, to simulate the impedance of a post-tensioned tendon 603. The steel strand of the tendon 603 had a 0.625 cm radius and was located along the longitudinal axis of the cylindrical section 600. Current injecting (or supply) electrodes 612, with a 0.8 cm radius, were placed on the surface of the grout electrolyte, 30 cm apart. The current injecting electrodes 612 were placed far enough from the ends of the tendon 603 to ensure there were no end effects. FIG. 6 illustrates an example of the mesh of the 3D model of the tendon assembly. The tendon 603 and current injecting electrodes 612 are seen as dark areas. As shown in FIG. 6, the mesh of the model contained tetrahedral elements which decreased in size at the electrode boundaries.

Results of the 4-point indirect impedance simulations are presented for a 3D uniform conductivity cylinder with and without a steel strand. A passive and an actively corroding steel was used in the model with multiple simulations of increasing grout resistivity to mimic the change in impedance as the grout cures. The range of values used for the grout resistivity was chosen to illustrate extreme effects.

Figure 7A:
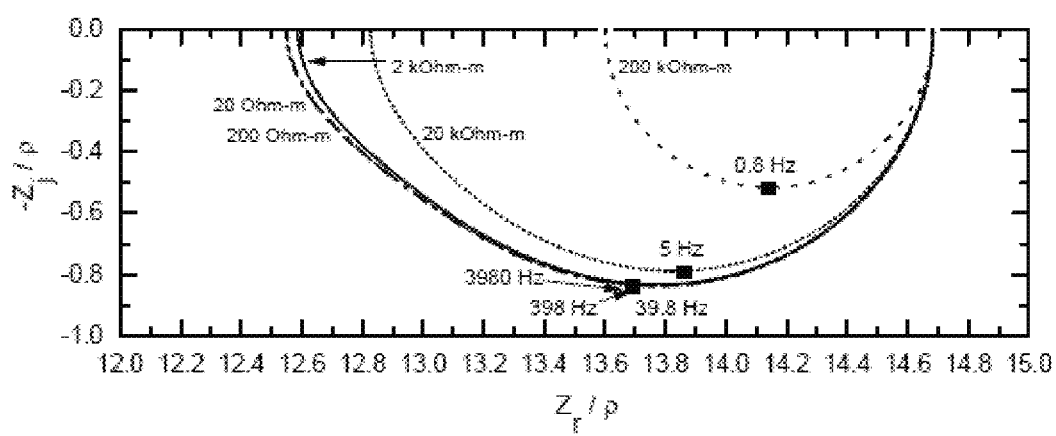
FIGS. 7A-15 are plots of various characteristics of a tendon assembly in accordance with various embodiments of the present disclosure.

The impedance was simulated for six different grout resistivities using a model without steel over a frequency range of 1 mHz-100 kHz. FIG. 7A shows a plot of an example of the simulated impedance response reduced by the grout resistivity of the 3D 60 cm long grout cylindrical section 600 with the grout resistivity as a parameter. At all resistivities, the impedance of FIG. 7A shows an inductive behavior. As the resistivity increases, the inductive loop forms a semi-circle.

Figure 7B:
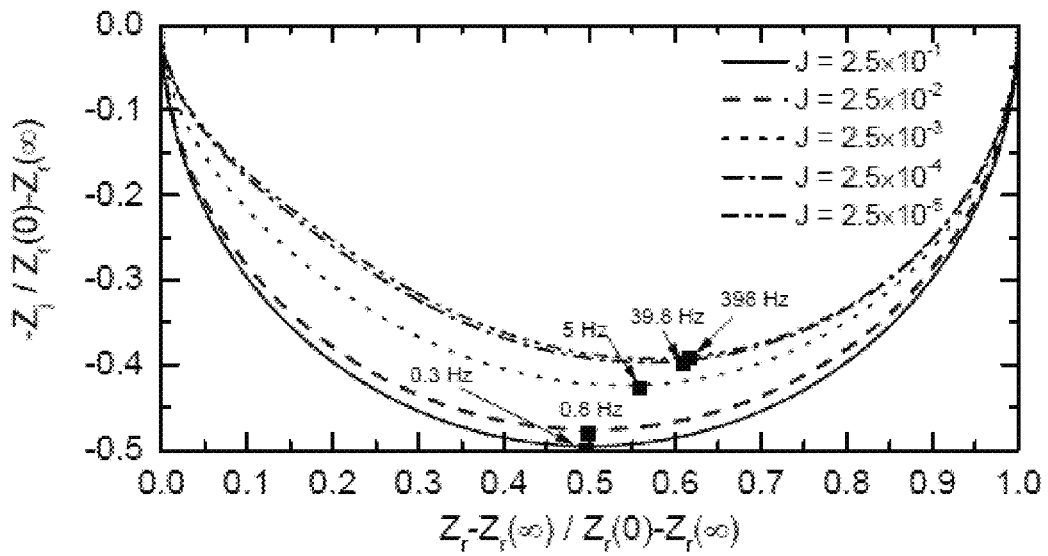

Another series of simulations were performed to show how the charge-transfer resistance at the current-injecting electrodes 612 (FIG. 6) contributes to the impedance. The grout resistivity was set to 200,000 Ohm-m and the exchange current density was increased by a factor of 10 for each simulation. As the exchange current density increases, the inductive loop becomes a semi-circle. The ratio J was calculated for each series using EQN. 12. The modified simulated impedance for both the modulation of the exchange current density and the grout resistance respectively is plotted in FIG. 7B. For each value of J, the shape of the inductive loop is the same in both series of simulations. Therefore, the impedance is dependent on the ratio of the grout resistance and the exchange current density. The inductive loop forms a semi-circle when J comes close to 1 and is deformed when it is much less than 1.

Figure 8:
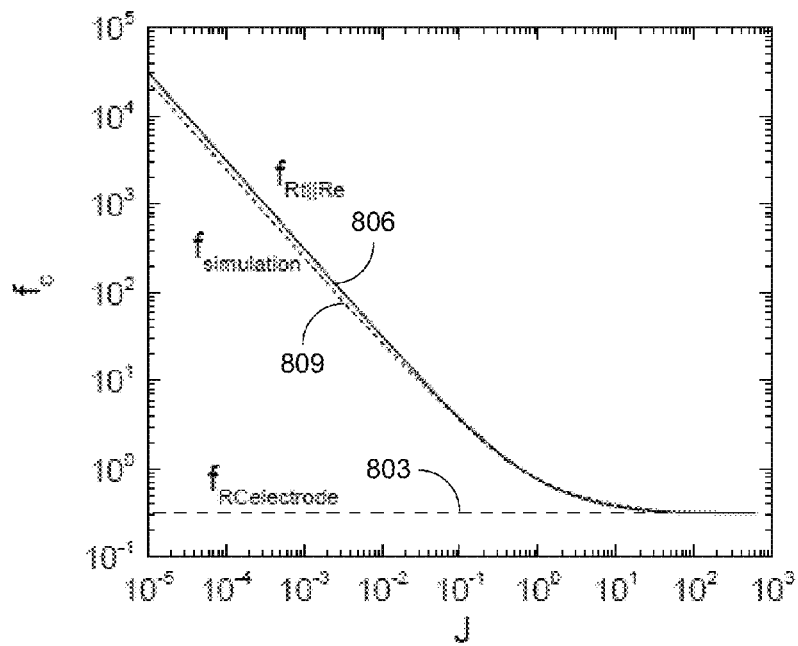

The characteristic frequency $$f = \frac{1}{2\pi RC} \tag{15}$$

based on the charge-transfer resistance (EQN. 14) and the double layer capacitance at the current-injecting electrodes 612 (FIG. 6) is used as a comparison to the characteristic frequency of the simulated results. The results for all electrolyte resistivities are plotted in FIG. 8 as a function of J. FIG. 8 illustrates an example of the characteristic frequency as a function of the ratio J. Also plotted is the characteristic frequency obtained from the effective resistance based on the parallel contribution of the electrolyte resistance and the charge-transfer resistance with the electrolyte resistance as the variable. Curve 803 ($f_{RCelectrode}$) refers to the characteristic frequency of the impedance of the charge-transfer resistance and the applied double layer capacitance at the current-injecting electrodes. Curve 806 ($f_{Rt||Re}$) refers to the characteristic frequency of the impedance of an RC element with an effective resistance based on the parallel contributions of the charge-transfer resistance at the electrodes and the grout resistance. Curve 809 ($f_{simulation}$) refers the characteristic frequency of the simulated impedance results. An effective length and cross-sectional area were assumed to obtain the electrolyte resistance from the resistivity. The results show that the characteristic frequency from the simulations is very close to the characteristic frequency calculated with an effective resistance of the charge-transfer resistance and the grout resistance in parallel. This suggests that the grout resistance acts in parallel to the electrode resistance.

Figure 9A:
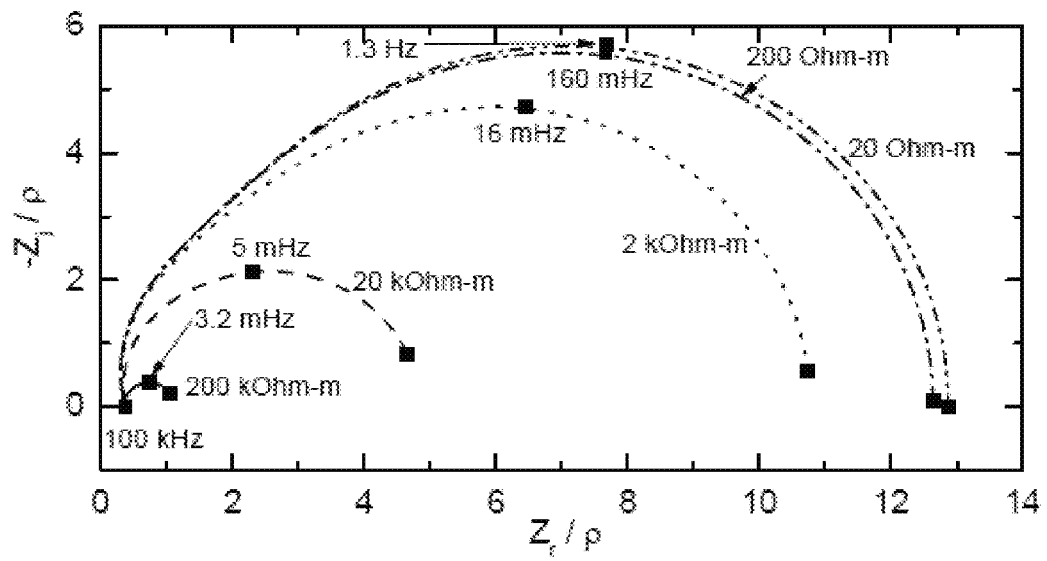

The simulated impedance scaled by the resistivity of the grout (ρ) from a model containing one active steel strand with the grout resistivity as a parameter was plotted. FIG. 9A show examples of the simulated impedance response reduced by the grout resistivity of a 3D 60 cm long grout cylindrical section 600 (FIG. 6) and a 0.625 cm radius actively corroding steel strand at the axis and a 0.625 cm radius passive steel strand at the axis, respectively, with the grout resistivity as a parameter. In FIG. 9A, the impedance shows a capacitive loop at lower frequencies while the inductive loop is still present at high frequencies. The impedance reduced by the grout resistivity shows that as the grout resistivity increases the capacitive loop is more of a semi-circle which can be attributed to the steel boundary condition.

Figure 9B:
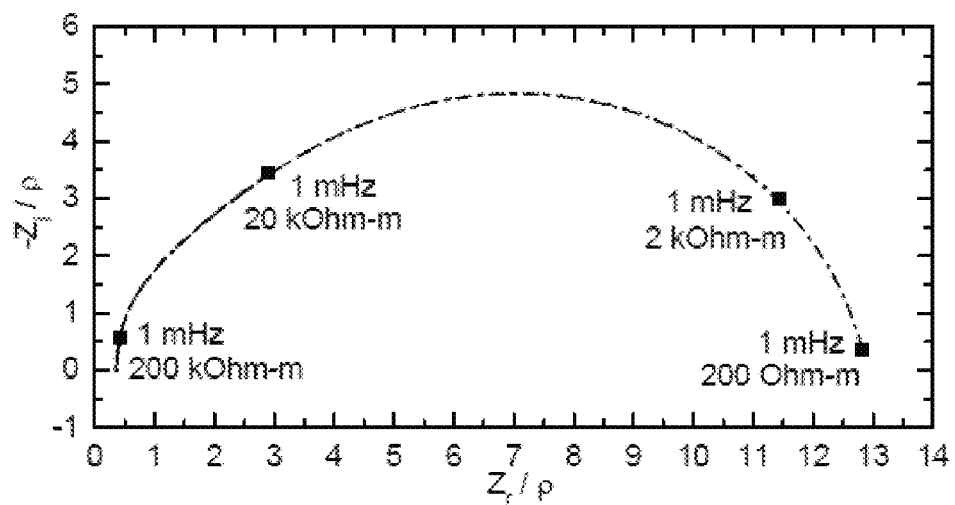

The simulated impedance of the case of a passive steel interface modeled as a CPE (Q=0.02 F/m2 and α=0.89) element is shown in FIG. 9B. In the case of the passive steel strand, the capacitive loop is depressed which could mean that the grout resistance acts in parallel with the CPE when the grout resistance is low. As the grout resistivity increases less of the full capacitive arc is visible within the range of frequencies simulated. The imaginary impedance of a CPE element approaches infinite as the frequency is decreased. This behavior becomes more apparent as the resistivity of the grout is increased.

Additional analysis was performed to obtain a deeper understanding of the simulation results. The phase and the magnitude of the impedance was observed as the steel corrosion rate was increased to determine which characteristics of the impedance can be associated with the steel. The magnitude of the absolute value of the imaginary impedance was assessed while increasing the current-electrode charge transfer resistance to determine how the characteristic frequencies are changed. Also an analysis of the zero-frequency limit of the impedance is shown with different electrode and grout parameters to reveal the effect of the charge-transfer resistance of the current-injecting electrodes on the simulated polarization resistance.

Figure 10A:
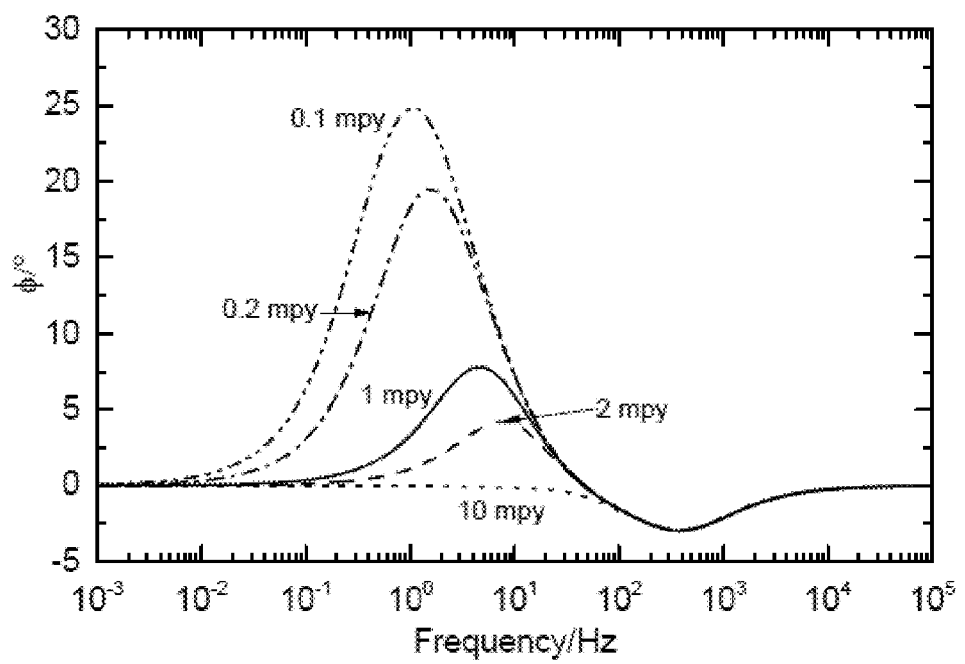
Figure 10B:
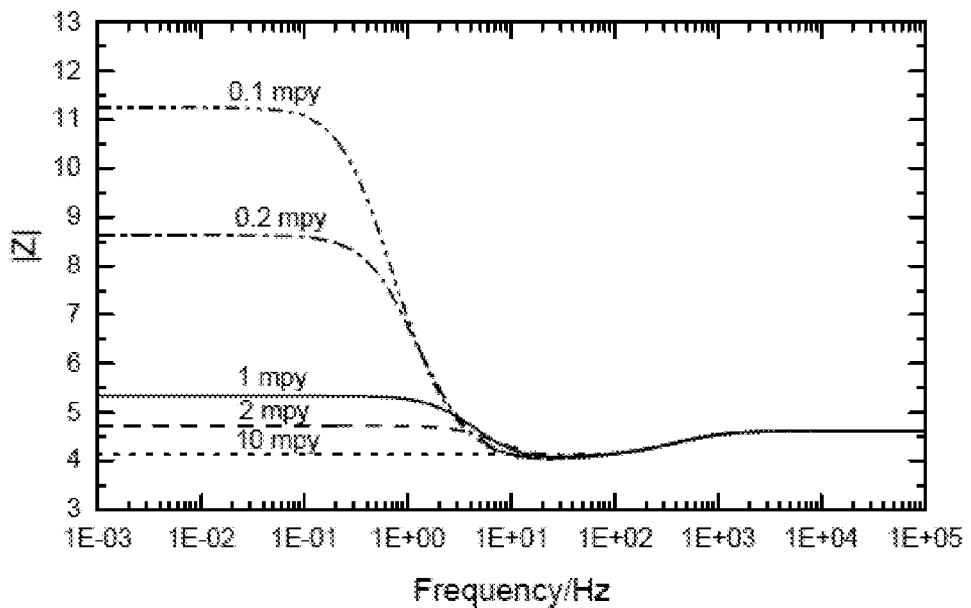

The phase and magnitude of the impedance simulations are plotted as a function of frequency with the steel polarization resistance as the variable in FIGS. 10A and 10B. FIGS. 10A and 10B illustrate an example of the phase angle and magnitude of the simulated impedance as a function of frequency with the steel corrosion rate as a parameter, respectively. Both figures show that the low frequency response is changed while the high frequency behavior remains the same. Therefore, the capacitive loop at low frequencies is a function of the steel interface.

Figure 11:
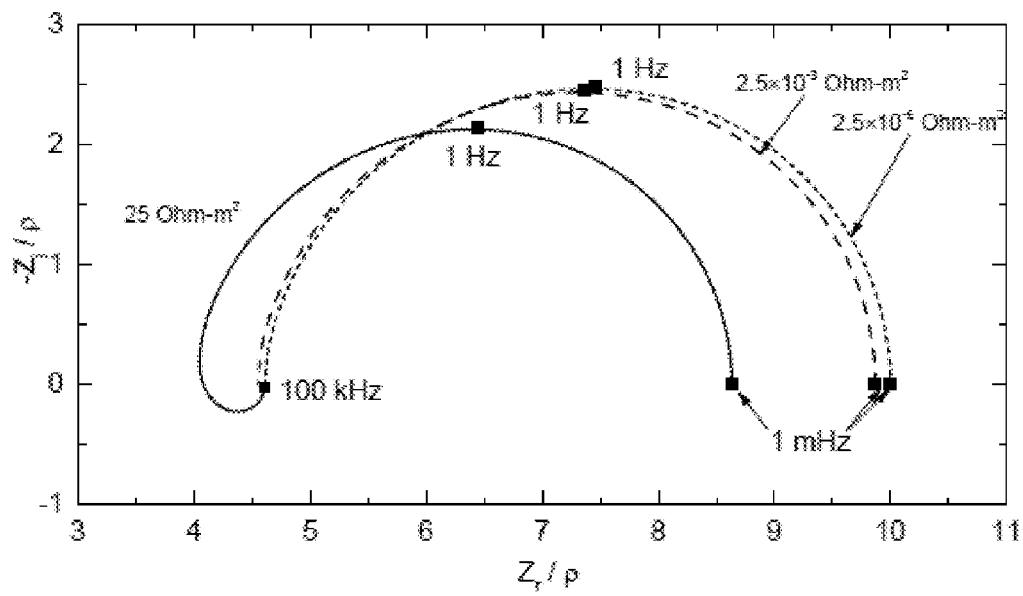
Figure 12:
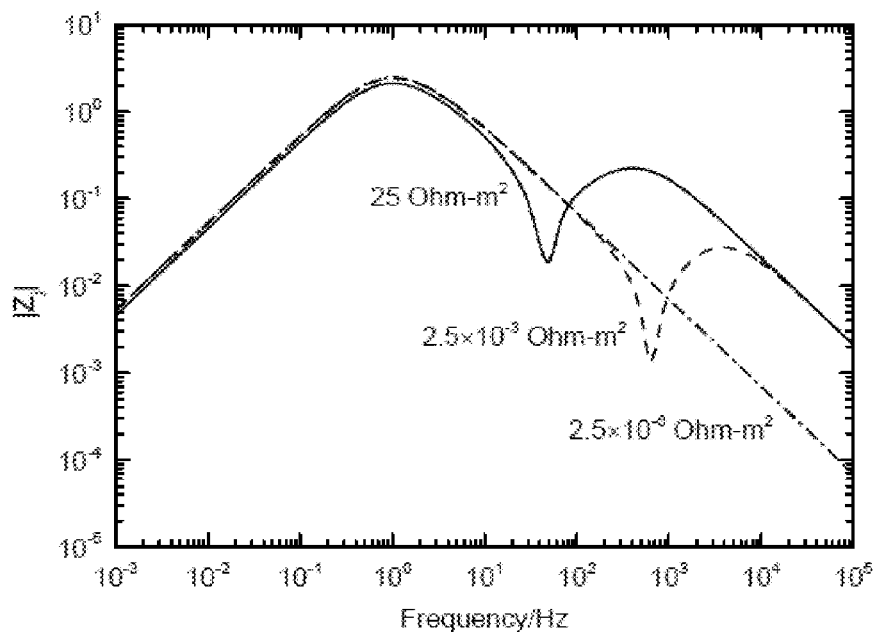

The simulated impedance response, scaled by the grout resistivity of the actively corroding steel strand, is presented in FIG. 11 with the charge-transfer resistance at the current injecting electrodes 612 (FIG. 6) as a parameter. The inductive loop at high frequencies decreases in size as the electrode charge-transfer resistance decreases. The zero-frequency limit of the real impedance is also decreased but not in a proportional fashion. The absolute value of the imaginary impedance is plotted in FIG. 12 as a function of frequency with the charge-transfer resistance at the current-injecting electrodes 612 as a parameter. The low-frequency time constant is unaffected by changes in the current-injecting electrodes' charge-transfer resistance. Only the high frequency time constant is changed. If the charge transfer resistance is extremely small, the high frequency inductive behavior due to this resistance is eliminated, and only the low frequency RC behavior is measured.

Figure 13:
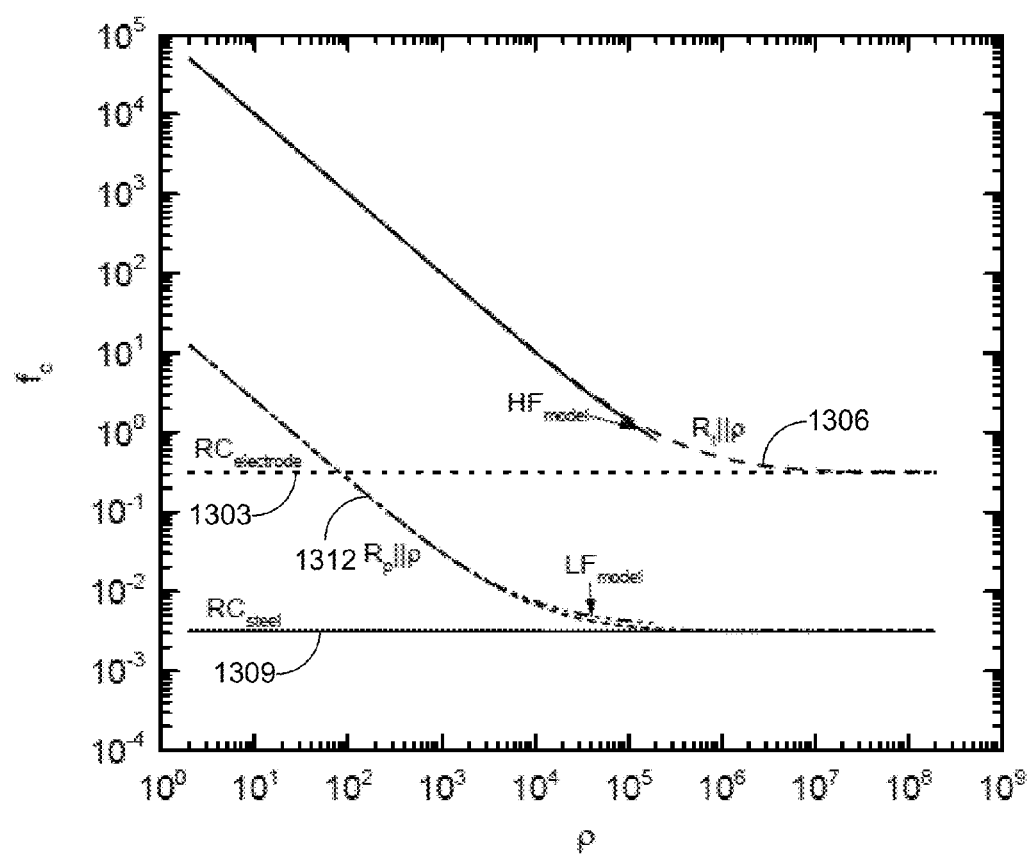

The characteristic frequencies associated with the high- and low-frequency time constants are plotted in FIG. 13 as a function of the grout resistivity. Curve 1303 ($RC_{electrode}$) refers to the characteristic frequency of the impedance of the charge-transfer resistance and the applied double layer capacitance at the current injecting electrodes. Curve 1306 ($R_e \| \rho$) refers to the characteristic frequency of the impedance of an RC element with an effective resistance based on the parallel contributions of the charge-transfer resistance at the electrodes and the grout resistivity. $HF_{model}$ refers the characteristic frequency of the simulated impedance results of the high frequency loop. Curve 1309 ($RC_{steel}$) refers to the characteristic frequency of the impedance of the polarization resistance and the applied double layer capacitance at the steel. Curve 1312 ($R_p \| \rho$) refers to the characteristic frequency of the impedance of an RC element with an effective resistance based on the parallel contributions of the charge-transfer polarization resistance at the electrodes and the grout resistivity. $LF_{model}$ refers the characteristic frequency of the simulated impedance results of the low frequency loop.

The high frequency behavior matches up with the characteristic frequency of an element with the charge-transfer resistance of the electrodes and the resistance of the grout in parallel to the double capacitance of the electrode interface. The characteristic frequencies of the capacitive loop match up with the characteristic frequencies of an element with the steel interface polarization resistance and the grout resistance in parallel with the double layer capacitance. The characteristic length used to calculate the resistance of the grout was the radius of the current injecting electrodes for the high frequency time constant and the distance between the current injecting electrodes for the low frequency time constant. The greater the grout resistance the more the impedance will be that of the RC behavior of the steel and the current injecting electrodes.

Figure 14:
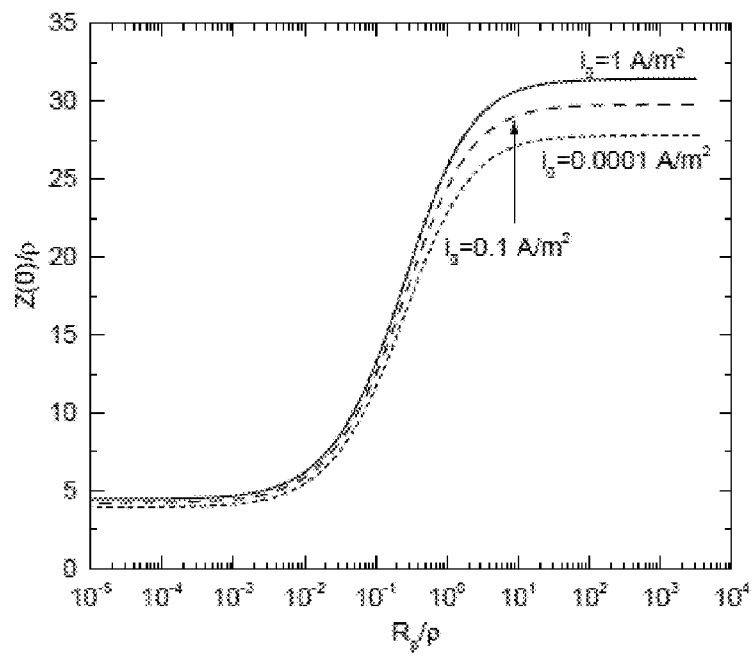
Figure 15:
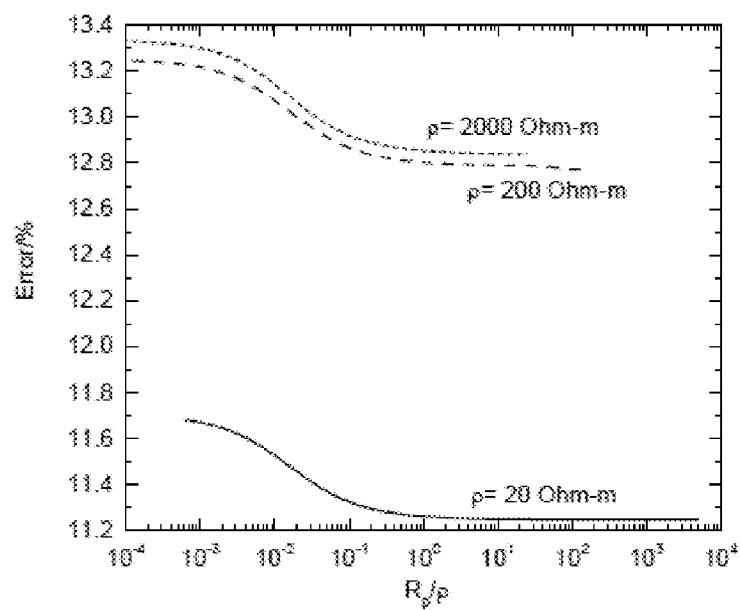

Referring to FIG. 14, the zero-frequency limit for a 2000 Ohm-m grout resistivity of the simulated impedance is plotted as a function of the ratio of the polarization resistance of the steel and the resistivity of the grout with the exchange current density of the current-injecting electrodes as a parameter. This relationship was independent of the grout resistivity. The high and low limits are due to the parallel and series contributions of the grout resistance to the polarization resistance. When the resistance at the current-injecting electrodes 612 (FIG. 6) is accounted for the zero frequency limit scaled down by the resistivity of the grout becomes a function the grout resistance, the steel polarization resistance, and the charge transfer resistance at the electrodes. The error in the zero frequency limit of the impedance where the charge-transfer resistance at the current-injecting electrodes is not taken into account is plotted in FIG. 15, assuming that the resistance is high enough that it fully affects the impedance. FIG. 15 illustrates the percent error of the difference between the zero frequency limit including the full contribution of the electrode charge-transfer resistance and the zero frequency limit. The error increases with increases in the resistivity of the grout and at 2000 Ohm-m the maximum error is 13.3 percent.

In the grout only simulations the simulated impedance showed inductive loops in all cases even though the applied boundary conditions at the electrode interfaces are of a charge-transfer resistance in parallel to a double layer capacitance. The characteristic frequencies of the inductive loops correspond to the characteristic frequencies of an element with the charge-transfer resistance and the grout resistance in parallel to the double layer capacitance. It is likely that the cause for the inductance is due to the non-uniform current distribution since this behavior was not present in the 2D case. When steel is placed into the model, also incorporating an RC interface, the simulated impedance showed the inductive loop at high frequencies and a capacitive loop at lower frequencies. The low- and high-frequency limits of the capacitive loop, which are used to determine the polarization resistance of the steel are effected by the current-injecting electrodes' contact resistance. This complicates the estimation of the true polarization resistance of the steel from the measured impedance. However, an analysis of the characteristic frequency can be useful in estimating the true polarization resistance of the steel as long as the grout resistance is known and a reasonable characteristic length is defined. It has been determined that the distance between the current injecting electrodes is a reasonable assumption for the low frequency time constant. Given a defined geometry and electrode configuration, simulations can be performed to match the experimental impedance. To obtain the true polarization resistance of the steel from the apparent polarization resistance it may be assumed that the resistance is constant over the steel surface, and the grout resistivity is constant through space.

The mathematical basis was shown for the use of electrode kinetics to simulate impedance. A model was made without any steel and it was determined that the ratio between the charge-transfer resistance at the current-injecting electrodes and the resistivity of the grout determines the impedance response. At all grout resistivities, the impedance was that of an inductive loop. When the ratio, J, is close to or greater than 1 the inductive loop is a semi-circle. When steel was placed into the model, the inductive behavior due to the current-injecting electrodes is still present and accompanied by a large capacitive loop whose limits were shown to be dependent on three parameters assuming a fixed electrode configuration and cell geometry. The parameters are the charge-transfer resistance at the current-injecting electrode, the grout resistivity, and the polarization resistance on the steel surface. At the characteristic frequency of each loop the impedance is indicative of the parallel contribution of the electrode resistance and the resistivity of the grout as shown in FIG. 13. It was shown that the use of boundary conditions that incorporate the charge-transfer resistance at the interface of the current-injecting electrode influences the impedance response and must be accounted for when estimating the true polarization resistance of the steel from the limits of the simulated impedance.

Referring back to FIG. 1, the total impedance ($Z_{total}$) can be measured at measurement points such as, e.g., sensor electrodes 121. As shown in FIG. 1, the impedance measured by the indirect technique can be described as expressed in EQN. 2 above. As mentioned above, the term $Z_{steel}$ includes the resistance to current flow in the metal of the tendon 103, which can normally be neglected. In addition, with proper selection of sensor electrode 121 location (e.g., between the supply or current injecting electrodes 112), $Z_{electrode}$ may also be neglected. Thus, the impedance measured by the contactless system can be expressed as:

$$Z_{total} = Z_{grout,1} + Z_{interface,1} + Z_{interface,2} + Z_{grout,2}. \quad (16)$$

With appropriate positioning of the sensor electrodes, the dominant impedance should be that of the steel-grout interface.

Rotating disk electrode experiments were used to develop an understanding of the interfacial impedance of the steel in terms of the chemical and electrochemical reactions, including the corrosion rates. Experiments were performed in an electrolyte intended to simulate the water composition inside the grout. The composition of the Simulated Pore Solution (SPS) was 2.0 g/L Ca(OH)2, 8.33 g/L NaOH, and 23.3 g/L KOH mixed in de-ionized water.

Rotating disk tips were fashioned from steel taken from a tendon 103. The corrosion potential was monitored for 24 hours in a simulated pore solution with a rotating speed of 100 rpm. The corrosion potential reached a stable value of −0.35 V (SCE) after 12 hours. Potentials were measured with reference to a Saturated Calomel Electrode (SCE). Linear sweep voltammetry was performed with rotating speeds of 100, 200, and 400 rpm at a scan rate of 10 mV/s. The rotating speed influenced the current at cathodic potentials, but did not affect the corrosion rate in a very wide range from −0.5V to 0.5V (SCE).

Impedance measurements were taken at rotation speeds of 100, 400 and 1600 rpm with a perturbation amplitude of 5 mV over a frequency range of 0.5-100,000 Hz in simulated pore solution. Impedance measurements were also taken at 400 rpm with a perturbation amplitude of 5 mV over a frequency range of 0.5-100,000 Hz in simulated pore solution adjusted with sulfuric acid to achieve pH values equal to 2.0, 5.5, 12.6 and 13.8. The experiment data showed that steel has good anti-corrosion ability in alkaline environments, however, when in the acidic environment, the corrosion rate increases significantly.

The stability of the tendon 103 in different environments was explored by use of Pourbaix diagrams generated by a computer program (CorrosionAnalyzer 1.3 Revision 1.3.33 by OLI Systems Inc), which uses an available database that takes into account non-ideal behavior not found in standard texts. For high pH values, the thermodynamically feasible products are $CaFe_2O_4$, $Mn_3O_4$ and $Fe(OH)^-_4$, while for low pH values, the thermodynamically feasible products are $MnSO_4$ and $Fe^{2+}$.

Figure 16A:
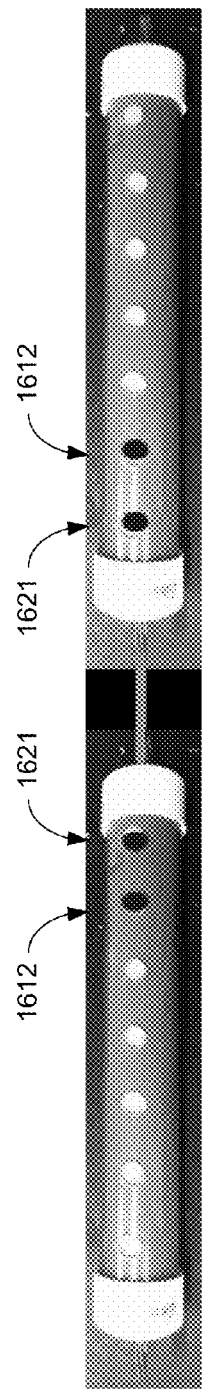
FIGS. 16A-16B and 18A-18B include images of tendon assembly samples or specimens used for testing in accordance with various embodiments of the present disclosure.

Experimental testing was carried out on tendon assembly samples or specimens, which include a section of tendon 103 extending through a duct 106, which is filled with grout 109. Openings were provided through the duct 106 to allow access to the grout 109. An experiment was set up in which the applied (or injected) current used to measure impedance was forced to go through the steel strand (tendon 103) located within the tendon assembly sample. This was done by connecting the steel strands of two tendon assembly samples together as is shown in FIG. 16A. The dark dots represent the location of the electrodes, where a current is applied between the first and fourth (supply) electrodes 1612 and the potential difference is measured between the second and third (sensor) electrodes 1621.

Figure 16B:
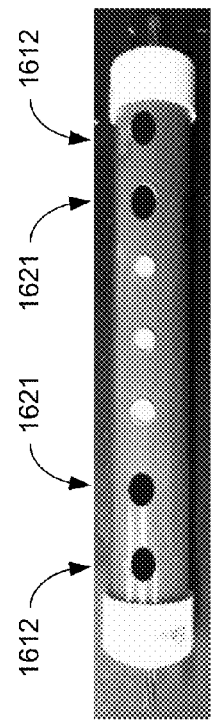
Figure 16C:
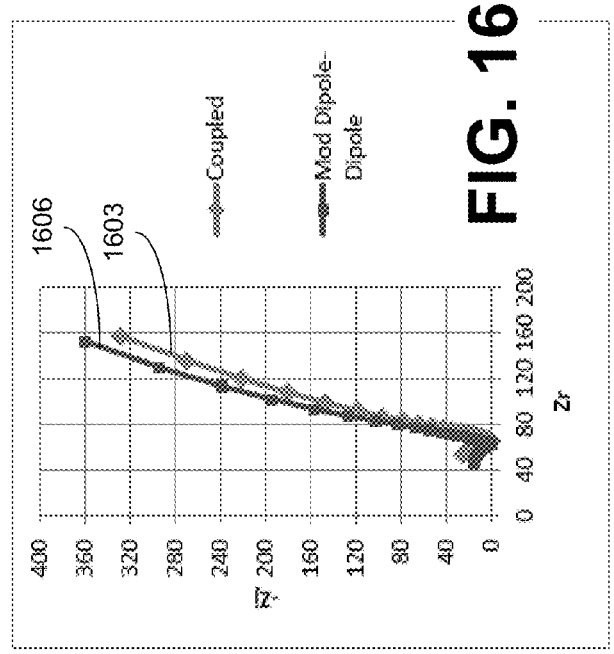

An objective of this experiment was to determine the electrode spacing that would allow for most of the applied current to go through the steel strand as opposed to the grout. Since the injected current takes the path of least resistance between the working and counter electrodes, the further the electrodes are placed apart from each other, the more likely the current will go through the steel. The result from the coupled configuration was compared to the result from an electrode configuration where electrodes were located at the ends of a single tendon assembly specimen as shown in FIG. 16B, which has an electrode configuration with 18.5 inches of separation between the outermost electrodes 1612. Referring to FIG. 16C, shown are a plot of the impedance response 1603 for the coupled configuration of FIG. 16A and a plot of the impedance response 1606 for the single sample configuration of FIG. 16B. Both plots 1603 and 1606 show equal ohmic resistances of approximately 65 ohms which should represent the resistance of the grout in both setups.

Other tests were performed to examine the sensitivity to cementitious properties. Half of the tendon assembly specimens were made with Sika 300Pt cable grout and the other half were made with Ordinary Portland Cement (OPC) with a w/c ratio of 0.45. Sika 300Pt grout is used in field tendon assemblies on the bridges and is designed to have a lower viscosity after mixing than ordinary Portland cement. It is also designed to have lower porosity and no shrinkage during curing. Each set of tendon assembly specimens included one control specimen which included one longitudinal axially located prestressing strand within the grout or cement and surrounded by a clear PVC duct. A second tendon assembly specimen was made with 3% chlorides added to the grout. A third tendon assembly specimen contained only grout or cement.

Tendon assembly specimens were tested with two different electrode configurations, the first electrode configuration is referred to as a Wenner array including 4 electrode contacts in line that are equally spaced. The electrode contacts were spaced at approximately 3 inch intervals. The second electrode configuration includes 3 inch spacing between the working (supply) electrode and first reference (sensor) electrode and the same for the second reference electrode (sensor) and the counter (supply) electrode. The spacing between the two reference (sensor) electrodes was approximately 9 inches. Larger spacing between the working and counter (supply) electrodes allows for more of the current to go through the steel of the tendon, which should be shown by larger capacitance values and larger arcs on the Nyquist plot if the steel is passive.

Figure 17B:
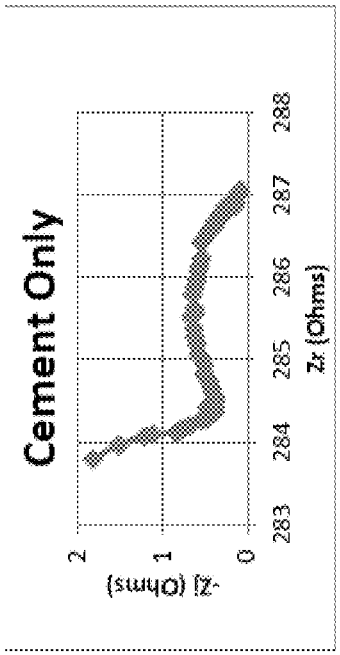
Figure 17A:
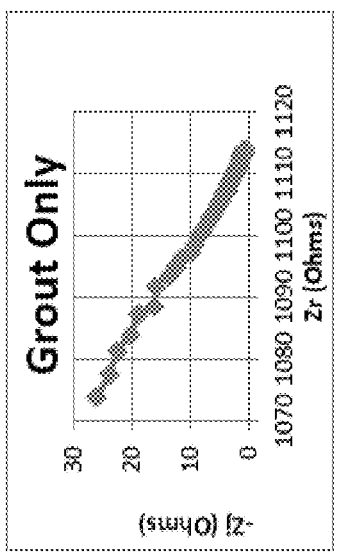

The Sika 300Pt grout provides more resistance than the OPC. This is shown in the two graphs of FIGS. 17A and 17B, which are examples of the impedance response from a tendon assembly specimen with grout only and cement only, respectively, and a Wenner array electrode configuration. The real impedance values for the grout (FIG. 17A) are almost four times as large as the cement (FIG. 17B). When measuring the resistance of a material based on impedance measurements it is the ideal situation to have current pass uniformly through the medium from parallel surfaces at a known distance apart. With the corrosion measurement system, this may not be achieved and therefore it is important to determine the path of the current so that we know what distance this resistance is determined from through modeling.

The distinguishing feature between grout with chlorides and grout without chlorides is that the arc in the Nyquist plot is smaller with the presence of chlorides. This means that the polarization resistance of the steel is lower when chlorides are present. This lower polarization resistance is usually seen at locations of corrosion.

Figure 18A:
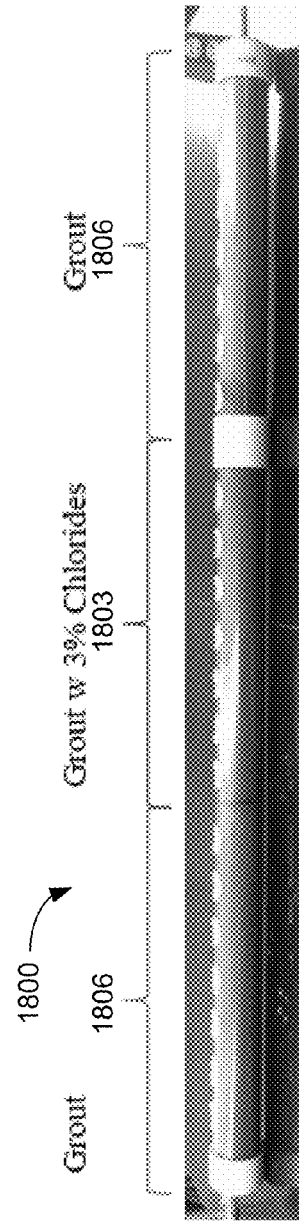
Figure 18B:
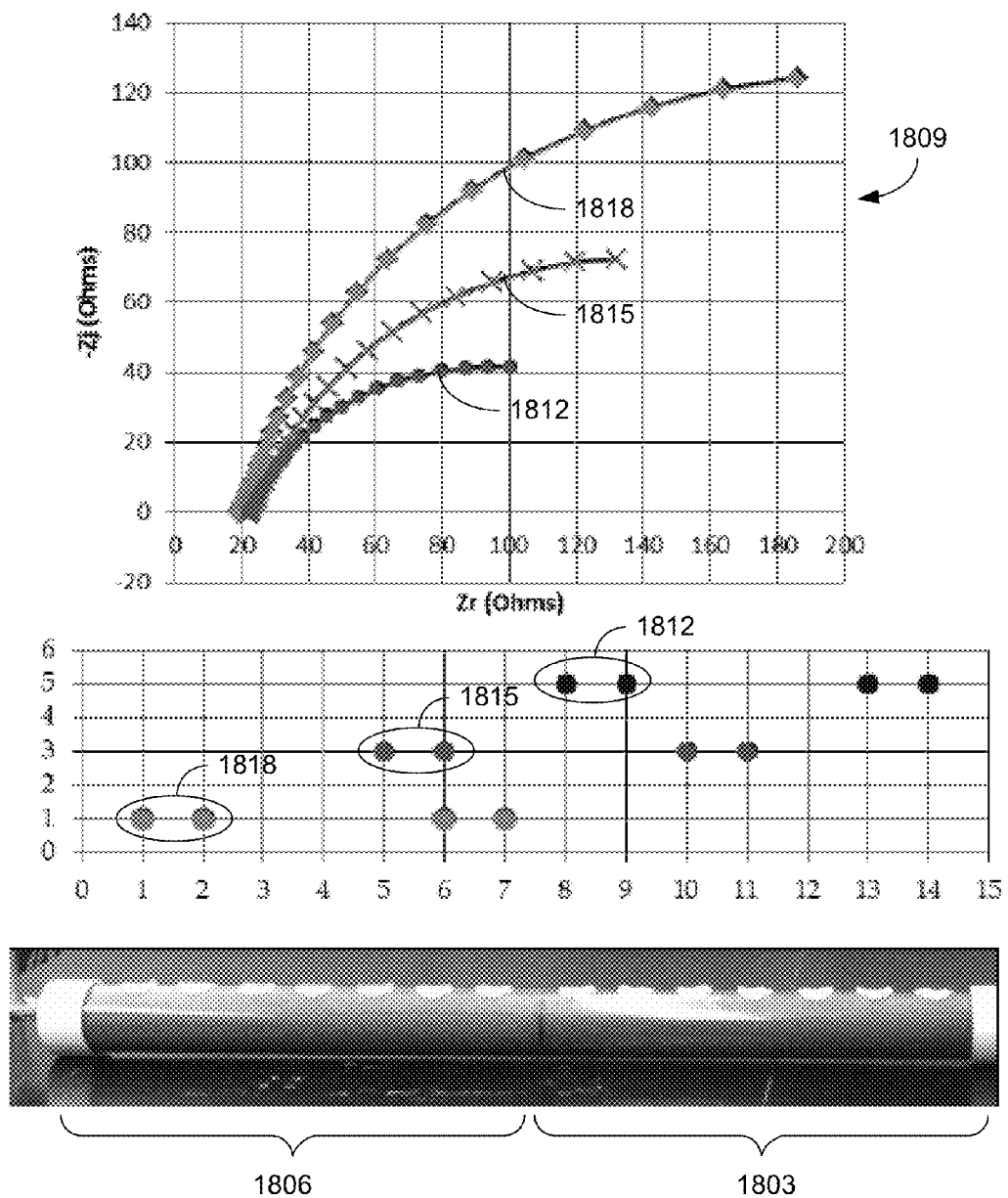

Referring to FIG. 18A, shown is a tendon assembly specimen 1800 with a length of 6 feet and a diameter of 3 inches. A 2 foot region 1803 in the center of the tendon assembly specimen 1800 included 3% chlorides to induce accelerated corrosion. By taking measurements at every 3 inch interval along the tendon assembly specimen 1800, it was shown that there is a clear difference in the capacitive behavior between the locations that did not include chlorides (regions 1806) and the locations that did (region 1803). The Nyquist plot 1809 of FIG. 18B shows an example of the impedance response of an 18.5 inch outermost electrode spacing along the 6 foot tendon assembly specimen 1800. FIG. 18B shows that, when all of the electrode contacts are placed in the region containing chlorides, the Nyquist plot 1809 indicates smaller polarization resistance and less capacitive behavior as seen in curve 1812. The lower plot in FIG. 18B represents the electrode locations for each corresponding Nyquist plots 1812, 1815 and 1818. Curve 1815 is the result from two electrodes being located in the no chlorides region 1806 and curve 1812 being located in the chloride region 1803. For curve 1818, the electrodes are in the no chlorides region 1806.

Figure 19:
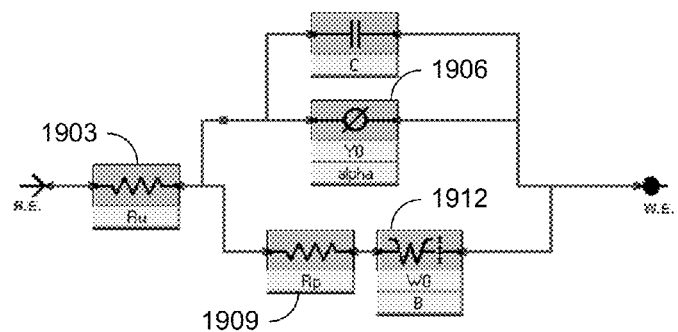
FIGS. 19 and 20 are circuits used to model the behavior of tendon assemblies in accordance with various embodiments of the present disclosure.

Referring next to FIG. 19, shown is an example of a model for three electrode impedance measurements in a simulated pore solution, where Ru 1903 stands for solution resistance, Y0 1906 and alpha account for the anodic reaction, and Rp 1909 and W0 1912 account for the cathodic reaction, which is influenced by mass transfer. This indicates that the steel is protected from corrosion in the simulated pore solution by a thin oxide layer. At lower pH values, the steel is subject to corrosion.

A brief data analysis was done to determine the dielectric properties of the cement based on the capacitive response in the high frequency region. This was done using two methods, the first graphically based and the second model based. The graphical method included plotting log frequency vs. log Zimag and taking the slope of the linear region within the high frequency range, which yields α, the exponent in a Constant-Phase-Element (CPE) model.

$$Z = \frac{R_e}{1 + (j\omega)^\alpha R_e Q}. \quad (17)$$

Figure 20:
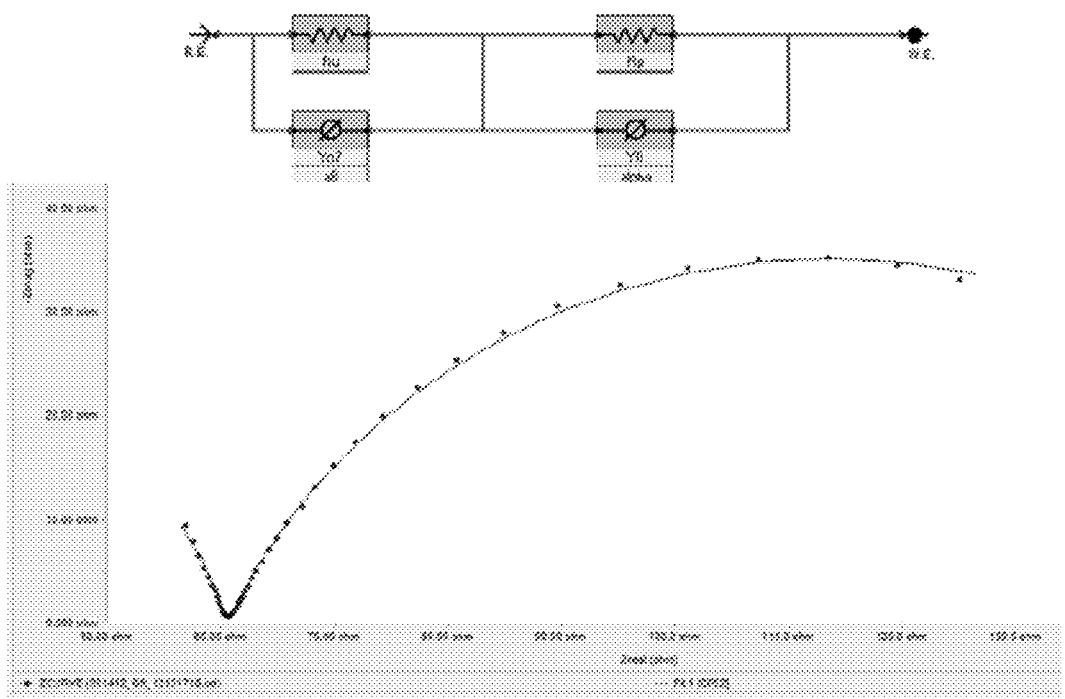

When α is equal to 1, the CPE parameter Q has units of capacitance. From these values and the geometry of the electrode configuration, a dielectric constant can be calculated using a power law model. Another way to determine these parameters is by using a model fitting method where electrical circuit components are set up to represent the behavior of our system. The circuit 2003 used to model the behavior of our samples is shown FIG. 20. By modeling the high frequency region as a CPE, the parameters can be extracted from the modeling software (Gamry E-Chem). Once again the power law model can be used to calculate the dielectric constant. The calculations gave values on the order of 20,000, which is much too large. Another CPE was fitted to the low-frequency portion indicated by the equivalent circuit. The two CPEs in series proved to be a good model for the tendon assembly samples, as can been seen by the agreement between the curve corresponding to the circuit 2003 and data plotted in the Nyquist plot 2006 of FIG. 20. The impedance response indicated by the plotted series is for an 18.5 inch spacing of the outermost electrodes where first two electrodes are in a chloride region and the last two are not. By fitting the impedance data to a circuit model, the type of behaviors and responses within the system. The true dielectric constant of a cementitious material is difficult to measure due to the presence of different phases. The use of high frequency ranges and a uniform current distribution can aid in the determination.

Corrosion of steel in grout may be attributed to: 1) decreases in pH, 2) contamination by chloride ions, and 3) lack of oxygen needed to form the protective oxide layers. The mechanism for iron dissolution in a chloride-free basic solution includes some absorbed intermediate reactant, while the mechanism for steel in the solution with chloride can be attributed to chemisorbed chloride ion displaced adsorbed water molecules followed by interaction with adjacently adsorbed hydroxyls. The pH value may decrease due to absorption of $CO_2$ or other acidic gases or by precipitation reactions for corrosion products that consume hydroxide ions. Corrosion can initiate in the form of pitting under conditions in which the local pH value is below 10. Chloride contamination is another serious issue for steel corrosion in grout. Pitting can occur when both chloride ion concentration and surface potential reach certain values. The importance of chloride ions in the steel corrosion in grout has led to the concept of a chloride threshold level, which can be expressed as the ratio of chloride and hydroxide ions, $[Cl^-]/[OH^-]$. However, the chloride threshold is very controversial and different values have been reported from 0.3 to 10. In the absence of dissolved oxygen, steel is not passivated in a highly alkaline environment.

Figure 21:
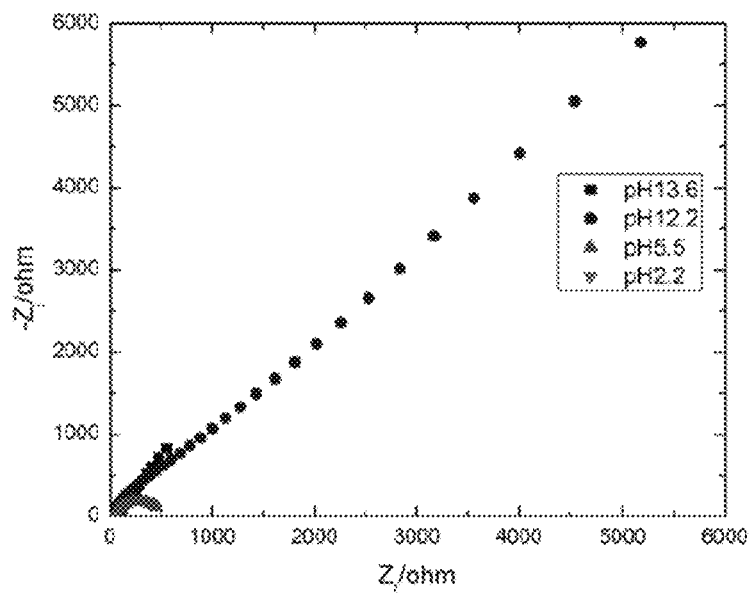

The effect of the pH value was examined. The pH value was changed from the original value of 13.6 to values of 12.6, 5.5, and 2.2. Using the rotating disk tips fashioned from steel taken from a tendon, impedance measurements were taken at a rotation speed of 1600 rpm and with a perturbation amplitude of 10 mV over a frequency range of 0.1 Hz-10 kHz at the open-circuit potential. FIG. 21 shows an example of impedance data for the rotating disk tip in SPs electrolyte with pH as a parameter. As can be seen in FIG. 21, the impedance data changed significantly as the pH value dropped and the impedance value reached a maximum when the pH value was 12.2.

Figure 22A:
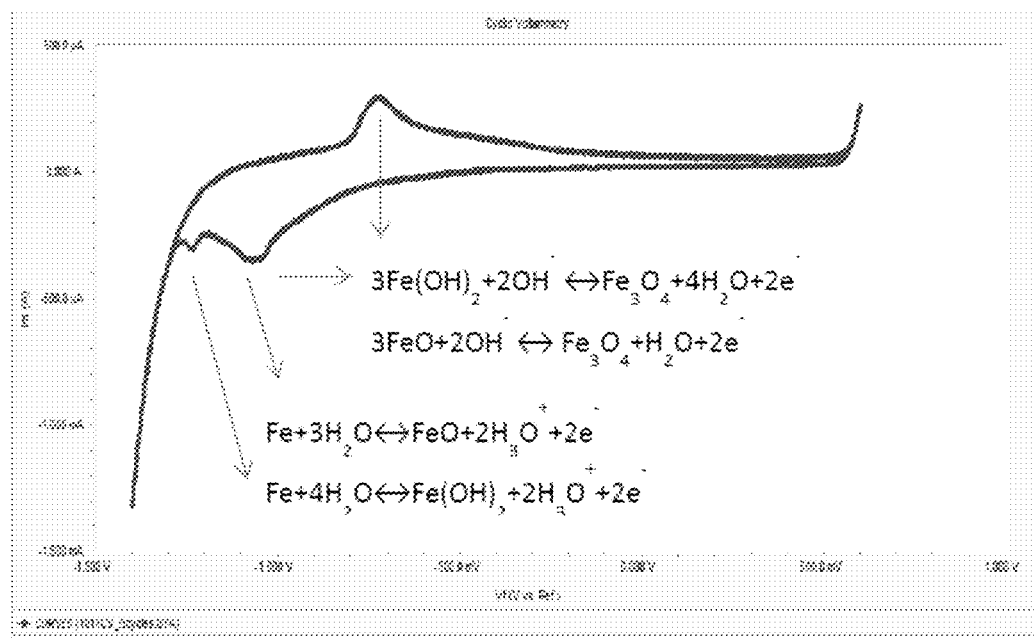
Figures 22B, 22C:
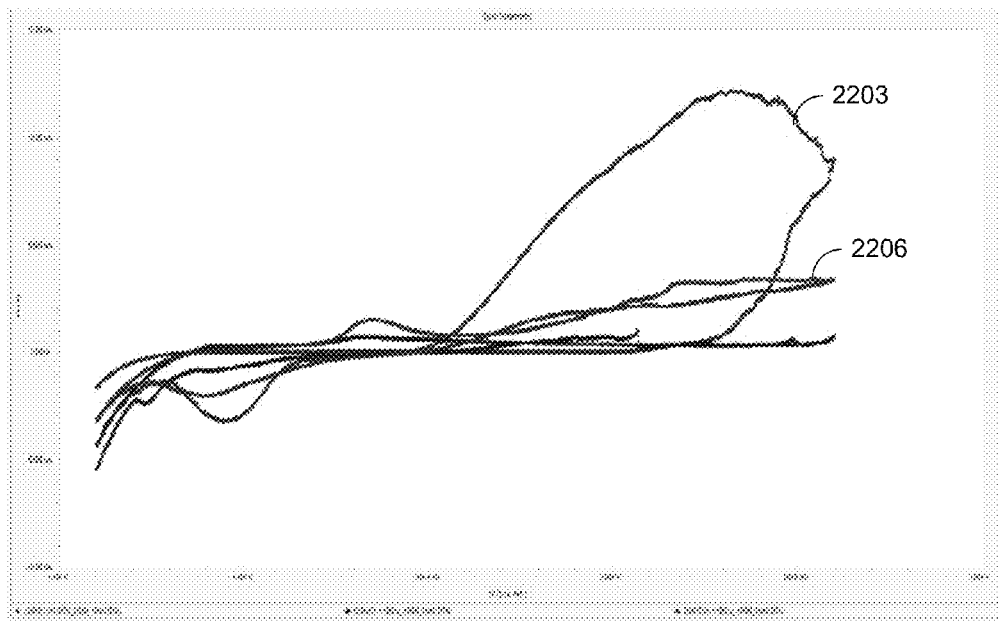

The influence of chloride contamination was explored by both cyclic voltammetry and impedance spectroscopy. Measurements were performed under both aerated and deaerated conditions. Cyclic voltammetry was performed with scan rates of 5, 10, and 50 mV/s from −1.4 to 0.6 V (SCE). The steel was conditioned at −1V (SCE) for 2000 seconds to remove any oxide that may have existed on the surface. The results of cyclic voltammetry are shown in FIGS. 22A-22C. FIG. 22A illustrates an example of the cyclic voltammogram for a stationary disk composed of tendon steel in $Cl^-$ free SPS electrolyte at a scan rate of 10 mV/s. The peak in FIG. 22A can be assigned to processes forming $Fe_3O_4$, FeO and $Fe(OH)_2$, as labeled in FIG. 22A. FIG. 22B shows the results for the stationary disk in a solution with 0.68M NaCl. Pitting clearly occurs during anodic processes of the first loop 2203, but, after forming iron compounds during the cathodic process, pitting cannot be seen in the second loop 2206. Therefore, the results support that $Fe_3O_4$, FeO and $Fe(OH)_2$ can form a protective film on the surface of steel. From the results shown in the table of FIG. 22C, pitting was observed for all measured scan rates for a chloride concentration of 0.68M, but was not observed for a concentration of 0.53M. As the hydroxide concentration was 0.32M, this work is consistent with a chloride/hydroxide ratio threshold equal to 2. The chloride content of the SPS electrolyte was fixed by adding NaCl.

Figure 23:
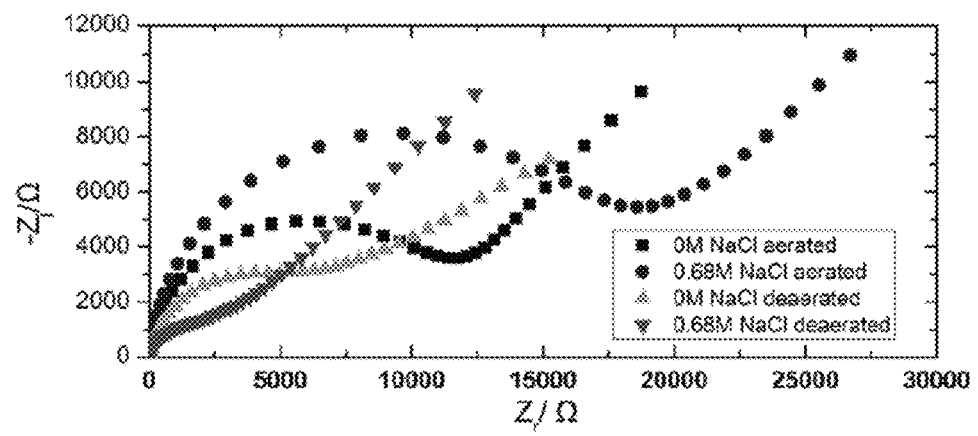
Figure 24:
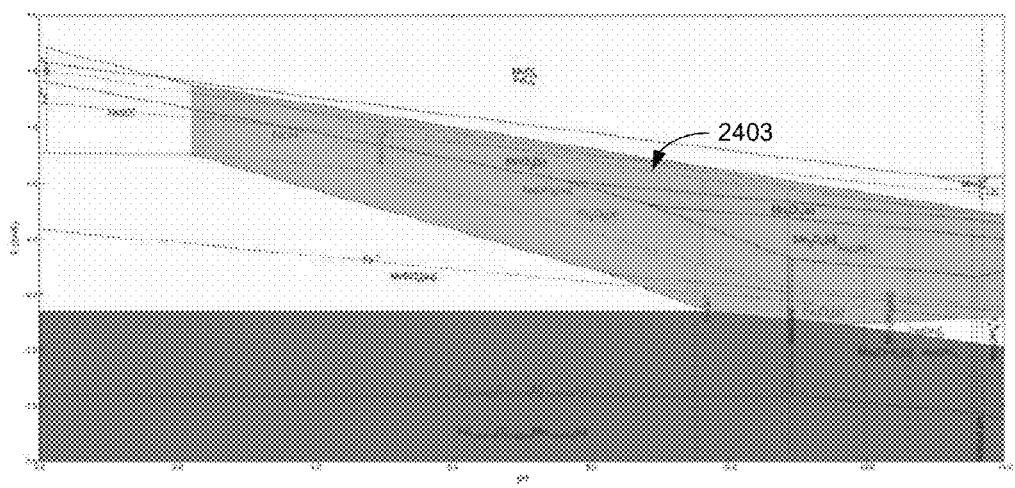

The influence of dissolved oxygen was explored by conducting experiments in both aerated SPS solutions and an SPS solution deaerated by nitrogen for one hour. Both the chloride-free and 0.68M NaCl solutions are used for experiments. Impedance measurements were taken for a stationary electrode with a perturbation amplitude of 10 mV over a frequency range of 10 mHz-100 kHz at open circuit potential. FIG. 23 illustrates an example of the impedance data for a stationary disk composed of tendon steel at open circuit in SPS electrolyte with state of aeration/deaeration and NaCl concentration as parameters. As shown in FIG. 23, the presence of chloride ions did not increase the corrosion rate in aerated solutions. In contrast, impedance results for deaerated solutions show that chloride ions did increase the corrosion rate. This result also supports the cyclic voltammetry results in which iron compounds were found to form a protective film on the surface of steel. The reason steel behaves actively in the highly alkaline environment and in the absence of oxygen can be explained by the Pourbaix diagram for carbon steel in SPS electrolyte, which is shown in FIG. 24. The diagram of FIG. 24 was generated using CorrosionAnalyzer 1.3 Rev. 1.3.33 by OLI Systems Inc. In the aerated solution, the corrosion potential can be maintained in the passive region (region 2403), but if the oxygen content is sufficiently small, the corrosion potential will decrease to the active region where only soluble compounds can be formed.

Figure 25A:
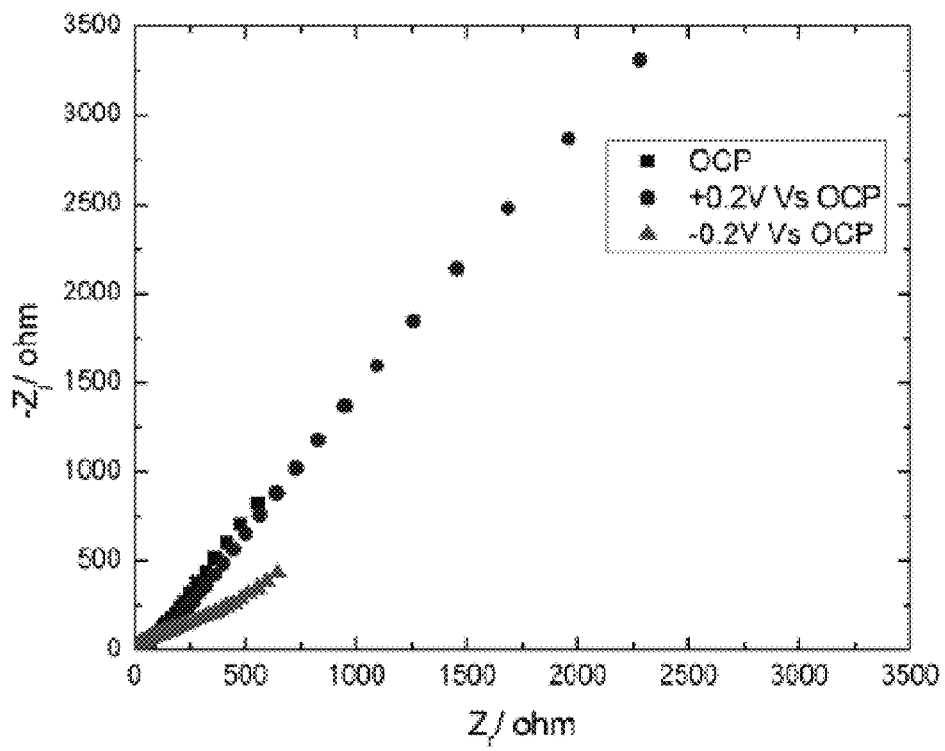
Figure 25B:
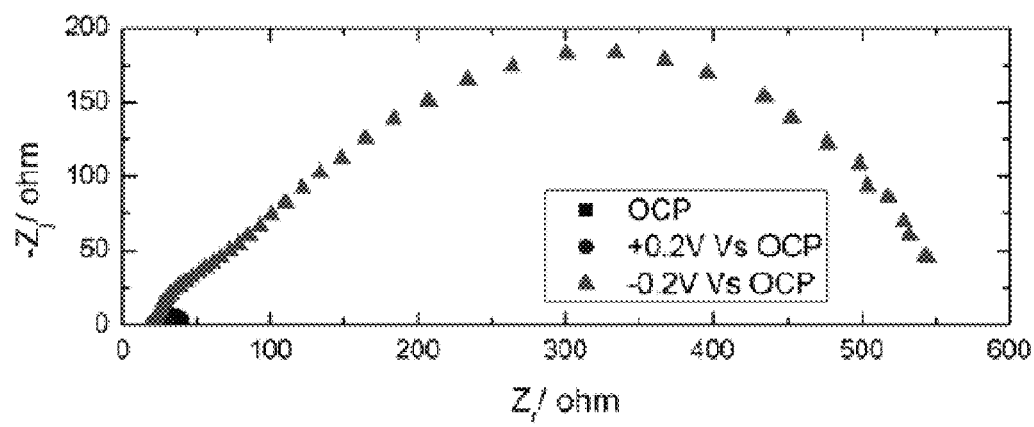

The question of whether the impedance response is dominated by anodic or cathodic reactions was answered by measuring the impedance at +0.2V and −0.2V versus open circuit potential and comparing the results to the impedance measurement at the open-circuit potential. FIGS. 25A and 25B show examples of impedance data for a disk composed of tendon steel rotating at 400 rpm in SPS electrolyte, with pH=13.6 and pH=2.2 respectively, with applied potential as a parameter. The results in FIGS. 25A and 25B show that, in a basic solution, the anodic reaction dominates the impedance response; whereas, in an acidic solution, the cathodic reaction dominates the impedance response.

Impedance measurements were taken at 0.1V and −0.1V with open circuit potential measurements taken in between. The results showed that the application of an anodic current increases the ohmic resistance of the system and, therefore, causes physical changes and can no longer be called a non-invasive technique. Since the ohmic resistance increased with the application of an anodic current the anodic reaction could include the reduction of water. To verify this, an attempt was made to measure the impedance multiple times at an anodic potential and see if the ohmic resistance continued to increase. Silver-silver chloride electrodes were used for the measurements. Referring to FIG. 26, shown is an example of the impedance results measured at the open circuit potential (OCP), an anodic potential (0.1 V), and a cathodic potential (−0.1 V). FIG. 26 shows the increase in ohmic resistance caused by the anodic DC current. The impedance at the open-circuit potential was more affected by the prior application of an anodic current than by a cathodic current.

To confirm that the addition of chloride accelerated corrosion, two synthetic tendon assemblies (each 2 feet in length) were cut at every electrode interval to determine the condition of the steel strand. One tendon assembly specimen contained Sika 300Pt grout and the other contained Sika 300Pt grout with 3% chlorides added as NaCl. An inverted-stage microscope was used to image the steel interface and to identify signs of corrosion. FIG. 27 includes (a) a visual image of a steel and grout interface of the tendon assembly specimen containing 3% chlorides and (b) a microscopic image of the steel and grout interface. It can be seen in the microscopic image of FIG. 27(b) that corrosion products have formed in a section located in the middle of the 2 foot specimen including grout that was contaminated with chlorides. As can be seen in visual image of FIG. 27(a), the corrosion was not visible by the naked eye.

Figure 28A:
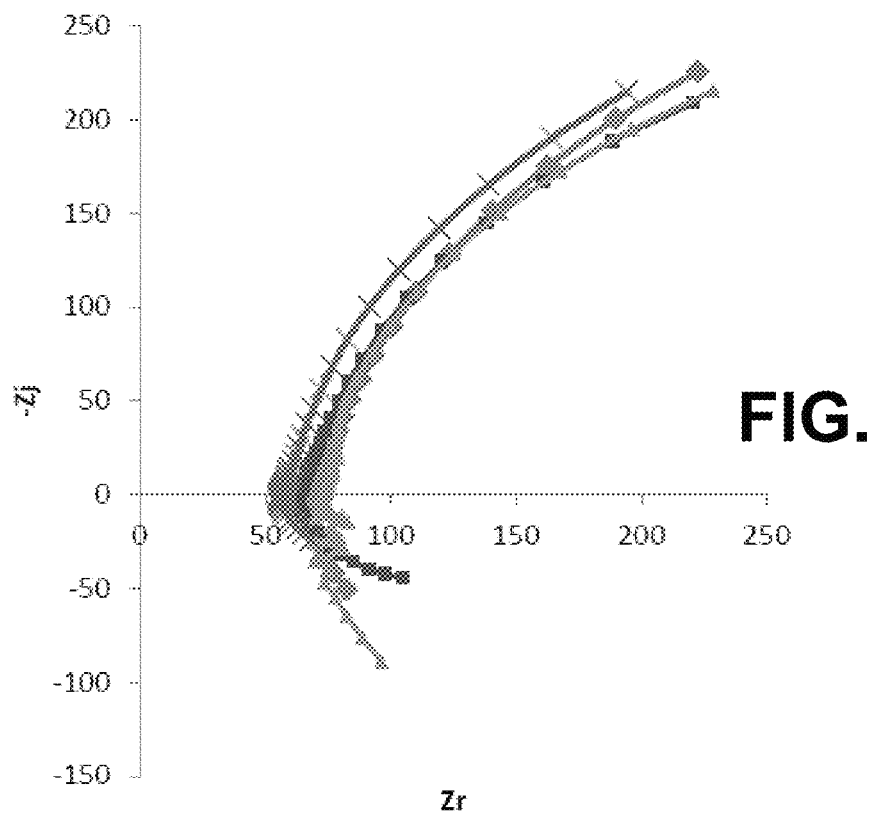
Figure 28B:
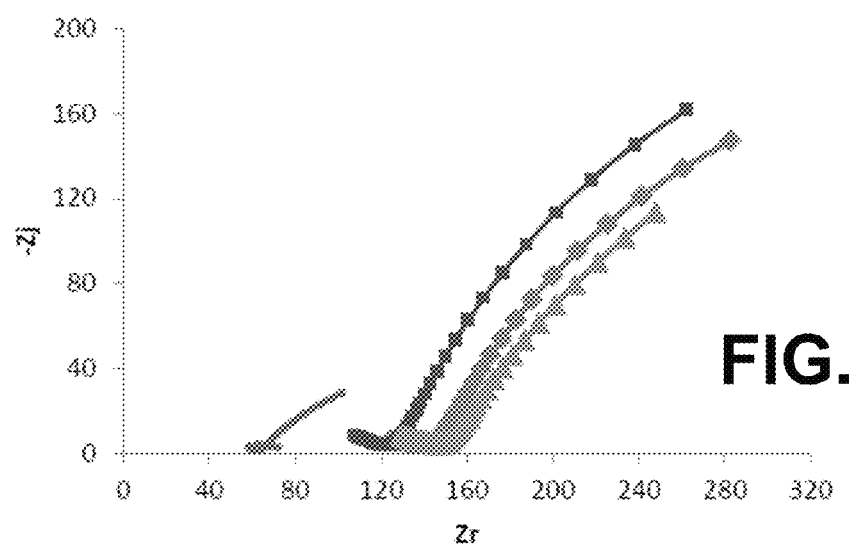

FIGS. 28A and 28B, respectively, show the impedance results for specimens without and with chloride ion contamination. FIGS. 28A and 28B show examples of the impedance response for a synthetic tendon strand with Sika 300Pt grout and with Sika 300Pt grout contaminated by the addition of 3 wt % chloride as NaCl, respectively. The different curves correspond to different positions along the 2 foot tendon assembly specimen. As shown in FIG. 28A, the impedance along the specimen without chloride contamination was independent of position. As shown in FIG. 28B, the specimen with the chloride contamination shows differences in impedance along the specimen. This suggests that changes in impedance can be associated with the presence of corrosion products.

A simplified current distribution model has been developed using Comsol Multiphysics software in both 2D and 3D. Initially, the steady state solution in 2D was solved using Laplace's equation to solve for the potential distribution through the grout under an applied potential and a simplified kinetic model of the steel interface. Two frequency-domain studies were also performed which included two different equivalent circuits to model the steel interface (R-C & CPE). 3D modeling was also initiated, using the same equivalent circuit models.

Figure 29A:
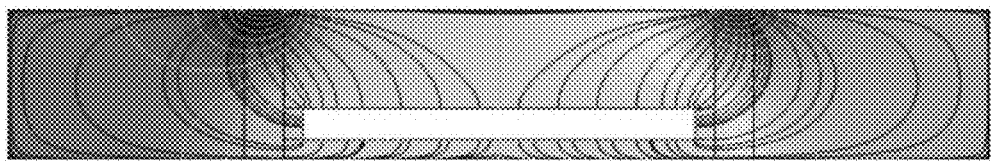
FIGS. 29A-29C and 31A-31B are 2D graphical representations of current and/or potential distributions within a simulated tendon assembly in accordance with various embodiments of the present disclosure.

To determine how the current flows through the system, the grout was treated as a homogenous material with a constant resistance. The Butler-Volmer equation was used to model the faradaic electrode kinetics. Two electrodes were placed at the top of the modeled specimen with an 18 cm spacing and with applied potentials of 1V and −1V, respectively. FIG. 29A shows an example of the 2D calculated steady-state current distribution using the Butler-Volmer equation to describe the electrode kinetics on the tendon strand. The simulations were performed using Comsol 4.3. The lines shown in FIG. 29A that intersect with the strand-grout interface represent the current flow, and the equipotential lines are shown perpendicular to the current flow. These results show that the steel is polarized indirectly through the application of a potential difference to the surface of the specimen.

Figure 29B:
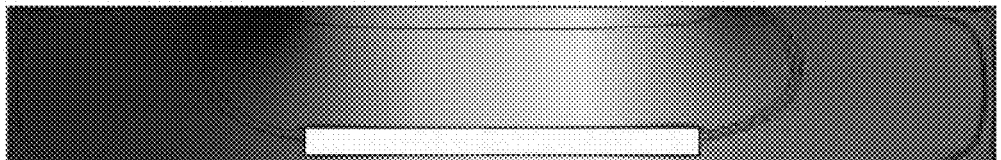
Figure 29C:

To obtain simulated impedance results, the analysis was done in the frequency domain over a range of frequencies that was large enough to pick up the full impedance response. When performing physical impedance measurements, a sinusoidal perturbation of constant amplitude is applied over a range of frequencies. To model this procedure, a constant value application of current can be used and the potential response measured. In this simplified model, the interface was assumed to behave according to the representation of an RC or an R-CPE element. The calculated 2D current distribution associated with low frequency impedance with an RC equivalent circuit behavior applied at the strand-grout interface is shown in FIG. 29B and the calculated 2D potential distribution associated with high frequency impedance with an RC equivalent circuit behavior applied at the strand-grout interface is shown in FIG. 29C. At low frequencies, the interface of the steel acts as an open circuit and the current flows around it. At higher frequencies the current behaves as a short circuit and the current enters the steel normal to the surface.

Referring to FIG. 30A, shown is a Nyquist plot obtained by placing two sensor (potential) probes on the surface of the grout of the tendon assembly model, between the source (current injection) electrodes with all four electrodes spaced equally from each other. The impedance was calculated at frequencies in the range of 0.01 Hz-10 k Hz by calculating the potential response as the difference between the two reference electrodes divided by the applied current difference between the working and counter electrodes. The full semicircle capacitive loop is indicative of an RC element. The charge transfer resistance was set to 500Ω and the capacitance was 0.01 F. The real and imaginary parts of the impedance are given in FIGS. 30B and 30C, respectively, as functions of the logarithm of frequency. As seen in FIG. 30A, the polarization resistance was approximately 325Ω.

Figure 31A:
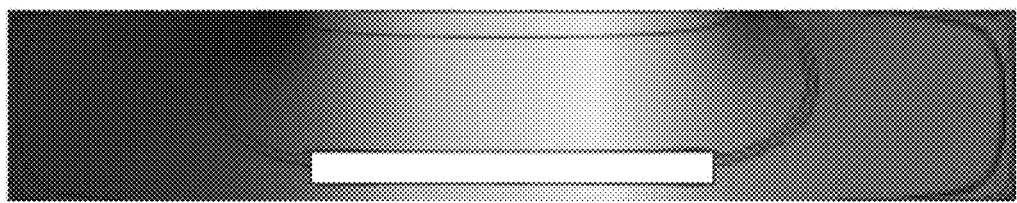
Figure 31B:

In the case of the interface represented by an R-CPE circuit the current distribution response values are almost identical to the R-C case. Once again, at low frequencies the current flows around the steel while at high frequencies the current flows to the steel and enters the steel normal to the surface. The calculated 2D current distribution associated with low frequency impedance with an R-CPE equivalent circuit behavior applied at the strand-grout interface is shown in FIG. 31A and the calculated 2D potential distribution associated with high frequency impedance with an R-CPE equivalent circuit behavior applied at the strand-grout interface is shown in FIG. 31B.

While the current distributions show similar behavior, the Nyquist plot was that of a depressed semi-circle which is indicative of an R-CPE circuit. The charge transfer resistance was set to 500Ω, and the CPE parameters were $\alpha=0.8$ and $Q=0.009$ $Fs^{\alpha}/cm^2$. The results obtained were similar to those shown in FIGS. 30A-30C, but the Nyquist plots showed a depressed semicircle and the real and imaginary impedances showed a more gradual change with frequency.

Figure 32:
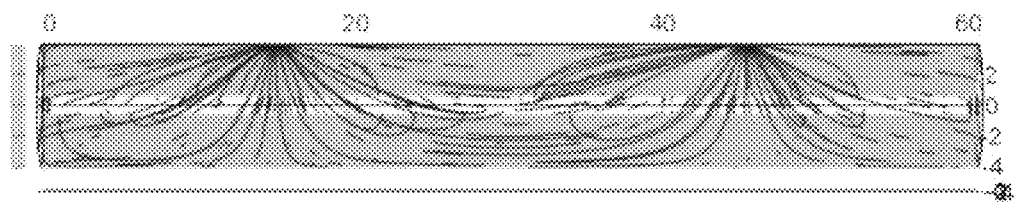
FIG. 32 is a 3D graphical representation of current distribution within a simulated tendon assembly in accordance with various embodiments of the present disclosure.
Figure 33A:
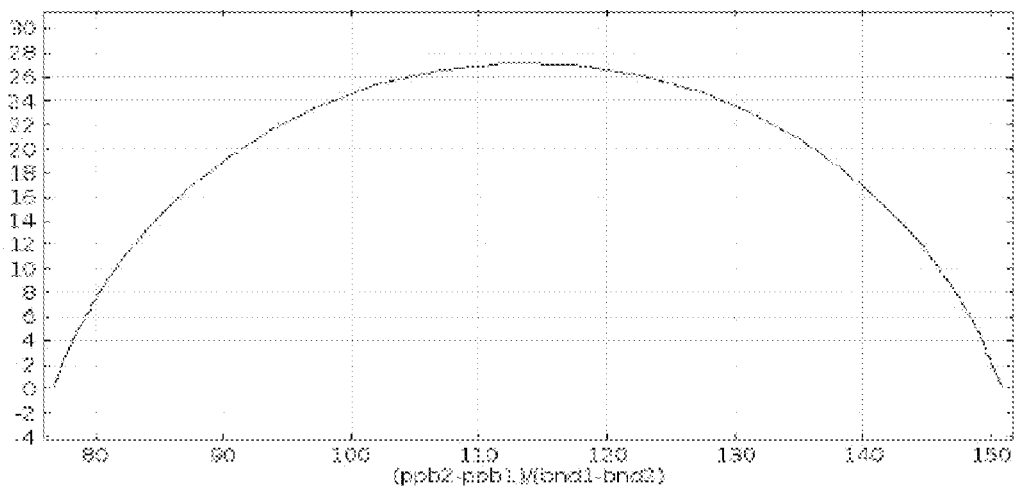
FIGS. 33A-33C are plots of the impedance of the simulated tendon assembly of FIG. 32 in accordance with various embodiments of the present disclosure.
Figure 33B:
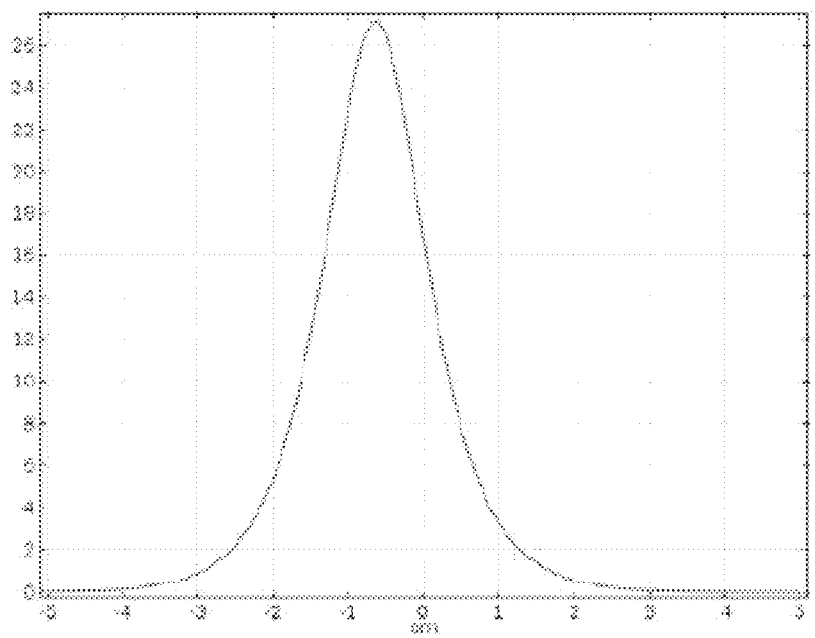
Figure 33C:
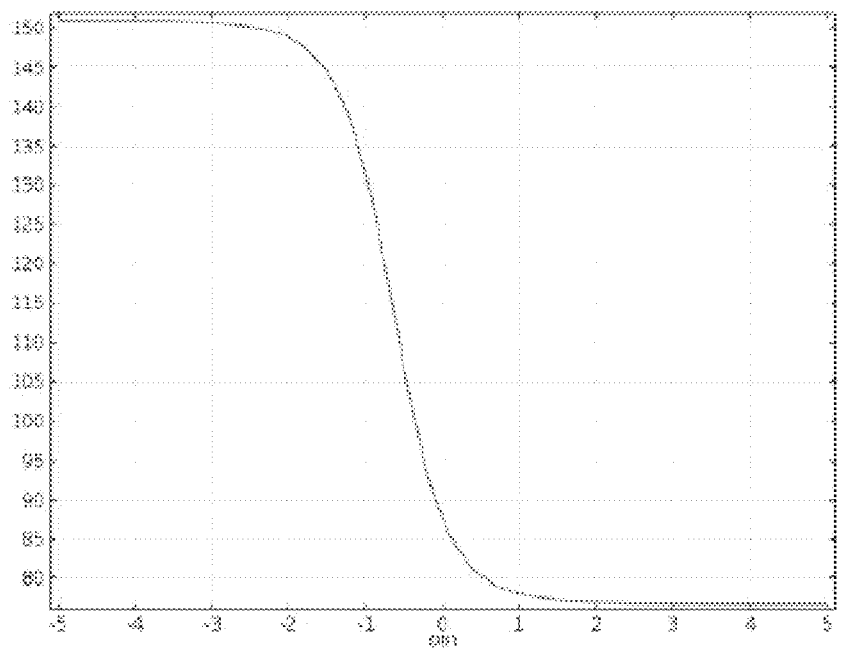

A 3D model was used to provide a more realistic representation of a tendon assembly. As was done for the 2D simulations, equivalent circuits were used as boundary conditions for the strand-grout interface. FIG. 32 is an example of the calculated 3D current distribution at low frequencies with R-CPE equivalent circuit behavior at the strand-grout interface. The current lines shown in FIG. 32 are wrapped around the strand, showing the more complex patterns that can be expected for the tendons. The corresponding impedance response is shown in Nyquist format in FIG. 33A and the real and imaginary parts of the impedance are given in FIGS. 33B and 33C, respectively.

Figure 34A:
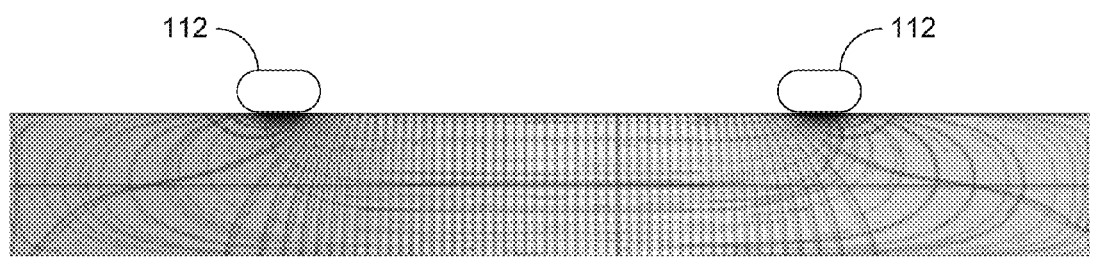
FIGS. 34A-34C are graphical representations of current and/or potential distributions within a simulated tendon assembly in accordance with various embodiments of the present disclosure.
Figure 34B:
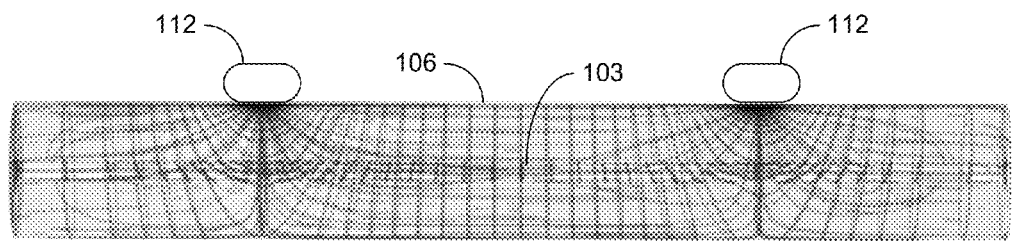
Figure 34C:
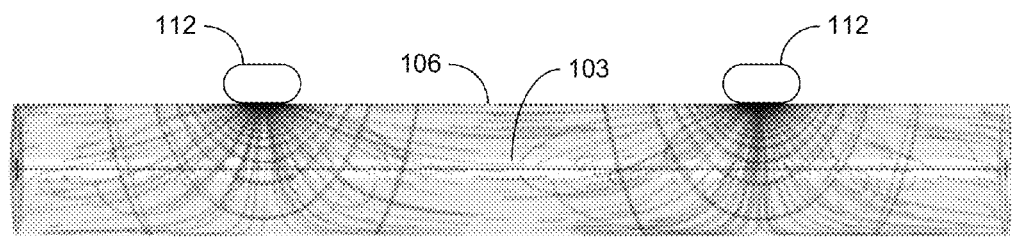

Referring next to FIG. 34A, show is a plot of the current flow through a cylindrical grout specimen obtained through numerical simulations and represented by the lines extending between the locations of the supply electrodes 112. The calculated potential distribution is expressed as a color (or shaded) gradient that is dependent on the frequency of the applied perturbation. In FIGS. 34B and 34C, the potential distribution through grout 106 containing a steel tendon 103 at different frequencies is provided. The presence of steel affects the potential distribution and therefore affects the impedance. The potential distribution is also dependent on the distance between the current-injecting electrodes 112, and the kinetics of the steel and grout interface. When the steel of the tendon 103 is in a passive state, an oxide film forms on the surface which protects it from corroding and also prevents current from flowing across the interface at low frequencies. When the steel of the tendon 103 is actively corroding, the reduction of iron provides a corrosion current which allows the applied current to flow across the interface. The two scenarios of current, either being blocked by a passive film or attacked by a corrosion current, influence the measured impedance. In the passive case, the impedance of the steel interface goes to infinity as the frequency goes to zero, which can be simulated by a Constant Phase Element (CPE). The parameters of the CPE can be used to estimate the film thickness. In the corroding case, the steel surface impedance is usually expressed as an RC element which consists of a polarization resistance, used to estimate the corrosion rate, and a double-layer capacitor.

The differences between the impedance of the tendon system containing passive or actively corroding steel may be determined. For the passive case, experiments were performed in which cylindrical tendon representations were made with one steel strand placed at the longitudinal axis of a grout cylinder encased in a PVC pipe. The impedance was measured using Ag/AgCl electrodes with a solid gel conductive adhesive to ensure contact to the grout. Finite element simulations were used to interpret the experimental results. The electrode kinetics was expressed as an oscillating current density as the summation of a charging and faradaic current given as:

$$\tilde{i} = j\omega C(\tilde{V} - \tilde{\Phi}) + \frac{(\alpha_a + \alpha_c)i_0 F}{RT}(\tilde{V} - \tilde{\Phi}) \quad (18)$$

The grout was modeled as a uniform conductivity media and Laplace's equation is used to solve for the potential distribution. The steel boundary condition is an oscillating current density representing the current across a CPE given as:

$$\tilde{i} = -\tilde{\phi}\omega^\alpha Q[\cos(\alpha\frac{\pi}{2}) + j\sin(\alpha\frac{\pi}{2})]. \quad (19)$$

Figure 35A:
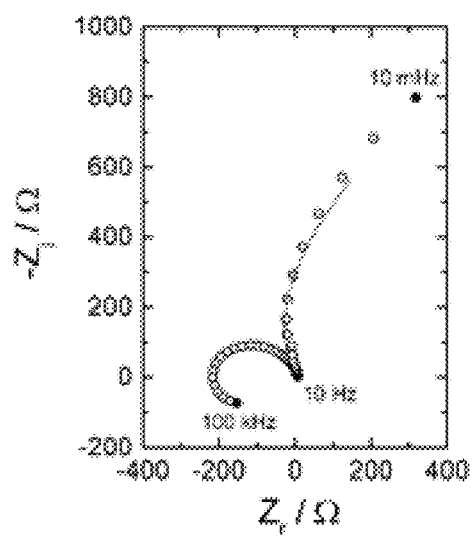
FIGS. 35A-35B are plots of experimental and simulation impedance for two different electrode configurations in accordance with various embodiments of the present disclosure.
Figure 35B:
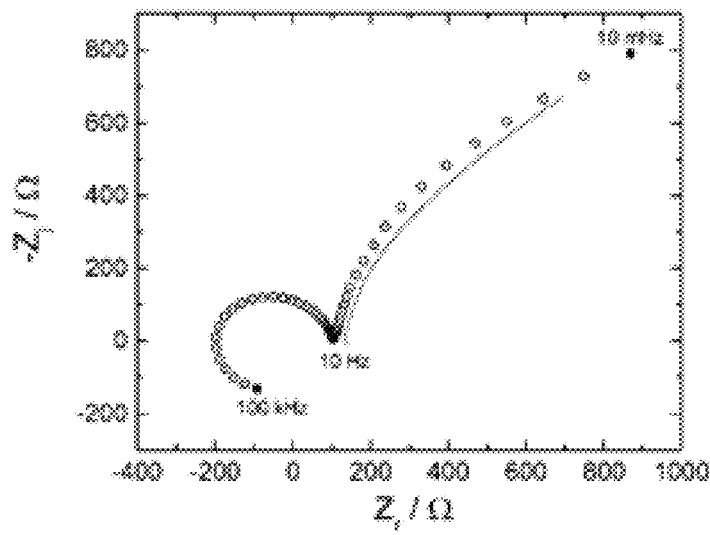

The impedance was simulated over a range of frequencies as the potential difference between two reference electrodes divided by the current of the working electrode. FIGS. 35A and 35B show plots of experimental and simulation impedance for two different electrode configurations: As shown in FIGS. 35A and 35B, the results are compared to experimental measurements with different electrode configurations. The electrode configuration used for the results in FIG. 35A includes the current-injecting electrodes 112 (FIG. 1) spaced at 18 inches and the reference electrodes 121 (FIG. 1) spaced at 12 inches. The electrode configuration for FIG. 35B includes the current injecting electrodes 112 spaced at 12 inches and the reference electrodes 121 spaced at 6 inches. In both cases the simulated impedance was close to the experimental impedance at low frequencies. Both plots exhibit similar shapes, where the impedance at low frequencies contains a contribution from the steel while the high frequency behavior is due mostly to the grout impedance. The effectiveness of this method relies on the use of accurate representations of the steel surface impedance. The impedance can be determined as a function of pH, temperature, and oxygen content.

Figure 36:
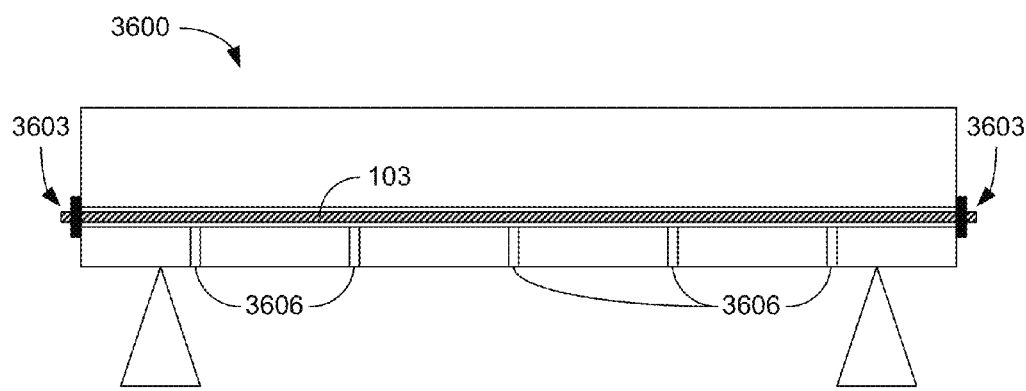
FIG. 36 is a graphical representation of a tendon assembly within a structure in accordance with various embodiments of the present disclosure.

Referring now to FIG. 36, shown is a graphical representation of an example of a structure 3600 including post-stressed tendons 103 in a tendon assembly such as that illustrated in FIG. 1. When the tendons 103 are included in a structure 3600 such as, e.g., a bridge span or support pillar, portions of the tendons 103 may be located within the structure 3600 while other portions may be accessible (e.g., at the anchor points 3603). Access openings 3606 may be located at appropriate locations through the surrounding material to allow for access to the grout 109 (FIG. 1) surrounding the tendons 103. For example, access openings 3606 may be drilled through the concrete of the structure 3600 at, e.g., inaccessible anchor points and/or low points where corrosion has a greater likelihood of occurrence. In other implementations, the access openings may be evenly distributed at predefined intervals along the length of the tendon 103 (e.g., every 6 inches, 12 inches, 18 inches, etc.) Probes may be inserted through the access openings 3606 to provide electrode contact with the grout 109 to supply current and/or make impedance measurements as previously discussed. In this way, corrosion of the tendons 109 may be detected without contacting or exposing the tendons 103. A series of measurements may be taken at different pulse frequencies to determine the Nyquest characteristics for evaluation of the tendon condition. Measurements may also be taken with different electrode contact spacing to allow a potential location of corrosion to be determined. A series of measurements can be taken along the tendon to determine the location of potential corrosion. In some cases, overlapping measurements may be used to identify the location of the corrosion.

The impedance measurement device 118 may include processing circuitry configured to determine an impedance of the tendon assembly based at least in part upon the current injected into the grout 109 via the source electrodes 112 and the potential measured across the sensor electrodes 121. A plurality of measurements may be taken over a range of frequencies to characterize the impedance of the tendon 103. The measurements may then be used to detect corrosion of the tendon 103 based at least in part the injected currents and measured potentials at different frequencies. Measurements may also be taken at a variety of locations to facilitate in determining the position of the corrosion. As shown in FIG. 36, a plurality of access openings 3606 may provide access to different locations on the tendon assembly for testing and evaluation. Probes including the source electrodes 112 and sensor electrodes 121 may be used to position the electrodes against the surface of the grout 109 for testing. The access openings 1403 may be drilled through the concrete of the structure and the duct 106 to allow access to the surface of the grout 109. In some embodiments, the impedance detection device may include a computing device to determine the condition of the tendon 103 based upon the measurements. For example, the impedance detection device may execute a program that obtains potential measurements at a plurality of frequencies and determines a condition of the tendon 103 based at least in part upon the potential measurements and the injected currents at the different frequencies.

The processing circuitry can include at least one processor circuit, for example, having a processor and a memory coupled to a local interface. To this end, the impedance measurement device 118 can comprise, for example, at least one computer or like device, which may be used to determine the condition of a tendon. Stored in the memory and executable by the processor may be a corrosion detection application that can determine the tendon condition based upon the voltage and current measurements. In this respect, the term "executable" means a program file that is in a form that can ultimately be run by the processor. The memory is defined herein as including both volatile and nonvolatile memory and data storage components. Volatile components are those that do not retain data values upon loss of power. Nonvolatile components are those that retain data upon a loss of power.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method, comprising:
injecting alternating currents through a portion of a tendon assembly including a tendon extending through a duct, the tendon at least partially encased in grout filling the duct, where access to a surface of the grout is established through small holes drilled into the duct, and four electrodes are placed into the small holes with a conductive gel to establish electrical contact with the grout, the four electrodes comprising a pair of supply electrodes and a pair of reference electrodes, where the alternating currents are injected over a range of frequencies through the pair of supply electrodes on the surface of the grout;
measuring potential differences across a portion of the grout surface between the pair of reference electrodes on the surface of the grout, the potential differences measured over the range of frequencies;
determining a total impedance ($Z_{total}$) based upon the injected alternating currents and the measured potential differences, the total impedance comprising:

$$Z_{total}=Z_{electrode,1}+Z_{grout,1}+Z_{interface,1}+Z_{steel}+Z_{interface,2}+Z_{grout,2}+Z_{electrode,2},$$

where $Z_{electrode}$ is an impedance associated with the electrical contact of each of the pair of supply electrodes in contact with the grout, $Z_{grout}$ is an impedance associated with the grout between each of the pair of supply electrodes and the tendon $Z_{interface}$ is an impedance associated with an interface between the grout and a surface of the tendon adjacent to each of the pair of supply electrodes, and $Z_{steel}$ is an impedance associated with the tendon; and
determining a condition of the tendon based at least in part upon the total impedance.

2. The method of claim 1, wherein the alternating currents are injected at a plurality of frequencies; and the potential differences are measured at the plurality of frequencies.

3. The method of claim 1, further comprising:
applying the pair of supply electrodes to the surface of the grout through the small holes with the conductive gel; and
applying the pair of reference electrodes to the surface of the grout through the small holes with the conductive gel.

4. The method of claim 1, wherein the condition of the tendon is associated with the impedance $Z_{interface}$ associated with the interface between the grout and the surface of the tendon.

5. The method of claim 1, further comprising:
injecting alternating currents through a second portion of the tendon assembly through small holes drilled into the duct, the small holes providing access to the surface of the grout;
measuring potential differences across a second portion of the surface of the grout between the pair of reference electrodes placed on the surface of the grout through small holes drilled into the duct; and
determining a second condition of the tendon based at least in part upon a second total impedance ($Z_{total}$) determined using the injected alternating currents and the measured potential differences associated with the second portion of the tendon assembly.

6. The method of claim 5, wherein part of the second portion overlaps part of the first portion of the tendon assembly.

7. A system, comprising:
a pair of supply electrodes configured to inject alternating currents through a portion of a tendon assembly including a tendon extending through a duct, the tendon at least partially encased in grout filling the duct, where access to a surface of the grout is established through small holes drilled into the duct, and where the pair of supply electrodes are placed into a first pair of small holes with a conductive gel to establish electrical contact with the grout and the alternating currents are injected over a range of frequencies through the pair of supply electrodes on the surface of the grout;
a pair of reference electrodes configured to measure potential differences across a portion of the surface of the grout between the pair of reference electrodes, where the pair of reference electrodes are placed into a second pair of small holes with a conductive gel to establish electrical contact with the grout, and the potential differences are measured over the range of frequencies; and
an impedance detection device configured to:
determine a total impedance ($Z_{total}$) based upon injected alternating currents and measured potential differences, the total impedance comprising:

$$Z_{total}=Z_{electrode,1}+Z_{grout,1}+Z_{interface,1}+Z_{steel}+Z_{interface,2}+Z_{grout,2}+Z_{electrode,2},$$

where $Z_{electrode}$ is an impedance associated with the electrical contact of each of the pair of supply electrodes in contact with the grout, $Z_{grout}$ is an impedance associated with the grout between each of the pair of supply electrodes and the tendon, $Z_{interface}$ is an impedance associated with an interface between the grout and a surface of the tendon adjacent to each of the pair of supply electrodes, and $Z_{steel}$ is an impedance associated with the tendon; and
determine a condition of the tendon based at least in part upon the total impedance.

8. The system of claim 7, further comprising a controllable power source configured to supply current at a plurality of frequencies via the supply electrodes.

9. The system of claim 8, wherein the impedance detection device is configured to determine the total impedance based at least in part upon the injected alternating currents and the potential differences measured at the plurality of frequencies.

10. The system of claim 7, further comprising probes including each of the pair of supply electrodes, the probes configured to extend through access openings passing through structural material surrounding the duct of the tendon assembly to allow each of the pair of supply electrodes to contact the surface of the grout through one of the first pair of small holes.

11. The system of claim 10, further comprising measurement probes including each of the pair of reference electrodes, the measurement probes configured to extend through access openings passing through the structural material surrounding the duct of the tendon assembly to allow each of the pair of reference electrodes to contact the surface of the grout through one of the second pair of small holes.

12. The system of claim 10, wherein a span of a bridge comprises the structural material surrounding the duct of the tendon assembly.

13. The system of claim 7, wherein the impedance detection device comprises processing circuitry configured to determine the total impedance and the condition of the tendon based at least in part upon the total impedance.

14. The system of claim 7, wherein the pair of supply electrodes and the pair of reference electrodes are silver-silver chloride electrodes.

* * * * *